US012350025B1

(12) United States Patent
Wang et al.

(10) Patent No.: US 12,350,025 B1
(45) Date of Patent: Jul. 8, 2025

(54) OPTICAL-BASED OSCILLOMETRY BLOOD PRESSURE MEASUREMENT DEVICE

(71) Applicant: Sharon Xiaorong Wang, Rancho Santa Margarita, CA (US)

(72) Inventors: Sharon Xiaorong Wang, Rancho Santa Margarita, CA (US); Jason Andrew Chen, Boston, CA (US); William Barry Chen-Mertens, Rendondo Beach, CA (US)

(73) Assignee: JB Health Tech, Rancho Santa Margarita, CA (US)

( * ) Notice: Subject to any disclaimer, the term of this patent is extended or adjusted under 35 U.S.C. 154(b) by 583 days.

(21) Appl. No.: 17/517,283

(22) Filed: Nov. 2, 2021

Related U.S. Application Data

(60) Provisional application No. 63/109,191, filed on Nov. 3, 2020.

(51) Int. Cl.
*A61B 5/022* (2006.01)
*A61B 5/00* (2006.01)
(Continued)

(52) U.S. Cl.
CPC ...... *A61B 5/02225* (2013.01); *A61B 5/02141* (2013.01); *A61B 5/02241* (2013.01);
(Continued)

(58) Field of Classification Search
CPC ............. A61B 5/0077; A61B 5/02116; A61B 5/02225; A61B 5/02416; A61B 5/0261; A61B 5/7278; A61B 2560/0462; A61B 2562/0204; A61B 2562/0238; A61B 2562/0247; A61B 5/02007; A61B 5/0205; A61B 5/02055; A61B 5/02108; A61B 5/02125; A61B 5/02141; A61B 5/02241; A61B 5/0225; A61B 5/02255;
(Continued)

(56) References Cited

U.S. PATENT DOCUMENTS 4,406,289 A 9/1983 Wesseling et al.
4,510,940 A 4/1985 Wesseling
(Continued)

FOREIGN PATENT DOCUMENTS

WO WO-2017009669 A1 * 1/2017 ........... A61B 5/0053

OTHER PUBLICATIONS

Smuts, J. (Mar. 7, 2011). PID Controllers Explained. Control Notes. https://blog.opticontrols.com/archives/344 (Year: 2011).*
(Continued)

*Primary Examiner* — Keith M Raymond
*Assistant Examiner* — Johnathan Maynard

(57) ABSTRACT

An optical-based oscillometric blood pressure measurement device includes a cuff, which is pneumatically connected to an inflation/deflation unit and electronically connected to a pressure detection unit. It also includes light emission diode and photodiode pairs, and a volume detection unit that converts the plethysmogram received by the photodiode to the optical oscilloetrygram as the artery volume signal. Its control unit determines inflation/deflation slopes and the start/stop pressures and accurately traces the prescribed controller set point. Its extraction unit measures the systolic, diastolic, and mean arterial pressure accurately.

20 Claims, 16 Drawing Sheets

(51) Int. Cl.
 A61B 5/021    (2006.01)
 A61B 5/0225   (2006.01)
 A61B 5/0235   (2006.01)
 A61B 5/024    (2006.01)
(52) U.S. Cl.
 CPC ........ *A61B 5/02255* (2013.01); *A61B 5/0235* (2013.01); *A61B 5/02416* (2013.01); *A61B 5/7225* (2013.01)
(58) Field of Classification Search
 CPC ............ A61B 5/02405; A61B 5/02438; A61B 5/0295; A61B 5/11; A61B 5/14551; A61B 5/318; A61B 5/6801; A61B 5/6802; A61B 5/6824; A61B 5/6826; A61B 5/6898; A61B 5/706; A61B 5/7217; A61B 5/7221; A61B 5/7264; A61B 5/7275; A61B 5/743; A61B 7/003
 See application file for complete search history.

(56) References Cited

U.S. PATENT DOCUMENTS

| | | | |
|---|---|---|---|
| 4,529,949 | A | 7/1985 | de Wit et al. |
| 4,539,997 | A | 9/1985 | Wesseling et al. |
| 4,846,189 | A * | 7/1989 | Sun .................... A61B 5/02255 600/480 |
| 6,669,648 | B1 | 12/2003 | Fortin et al. |
| 7,390,301 | B2 | 6/2008 | Skrabal et al. |
| 7,783,345 | B2 | 8/2010 | Skrabal et al. |
| 8,114,025 | B2 | 2/2012 | Fortin et al. |
| 8,343,062 | B2 | 1/2013 | Fortin et al. |
| 8,641,632 | B2 | 2/2014 | Quintin et al. |
| 8,798,703 | B2 | 8/2014 | Huber et al. |
| 8,814,800 | B2 | 8/2014 | Fortin et al. |
| 9,615,756 | B2 | 4/2017 | Mills et al. |
| 9,974,448 | B2 | 5/2018 | Mills et al. |
| 10,098,554 | B2 | 10/2018 | Fortin |
| 10,285,599 | B2 | 5/2019 | Fortin |
| 2010/0152600 | A1* | 6/2010 | Droitcour ............ A61B 5/7221 600/534 |
| 2016/0220195 | A1* | 8/2016 | Abu-Tarif ............ A61B 5/7278 |
| 2018/0289271 | A1* | 10/2018 | Axelrod ............... A61B 5/6824 |
| 2019/0008399 | A1* | 1/2019 | Mukkamala ......... A61B 5/0261 |
| 2019/0053768 | A1* | 2/2019 | Enari ................. A61B 5/02108 |
| 2020/0305740 | A1 | 10/2020 | Quan et al. |
| 2022/0313098 | A1* | 10/2022 | LeBoeuf ............. A61B 5/7221 |

OTHER PUBLICATIONS

Chen, S. (2010). Improving algorithms for oscillometric blood pressure estimation by suppressing breathing effects (Doctoral dissertation, University of Ottawa (Canada)). (Year: 2010).*

Aboy, M., McNames, J., Hornero, R., Thong, T., Cuesta, D., Novak, D., & Goldstein, B. (Sep. 2004). A novel statistical model for simulation of arterial and intracranial pressure. The 26th Annual International Conference of the IEEE Engineering in Medicine and Biology Society. vol. 1, pp. 129-132 (Year: 2004).*

Staats, C., Austin, D., & Aboy, M. (2008). A statistical model and simulator for cardiovascular pressure signals. Proceedings of the Institution of Mechanical Engineers, Part H: Journal of Engineering in Medicine, 222(6), 991-998. (Year: 2008).*

McNames, J., & Aboy, M. (Aug. 2006). Cardiovascular signal decomposition and estimation with the extended Kalman smoother. In 2006 International Conference of the IEEE Engineering in Medicine and Biology Society (pp. 3708-3711). IEEE. (Year: 2006).*

McNames, J., & Aboy, M. (2007). Statistical modeling of cardiovascular signals and parameter estimation based on the extended Kalman filter. IEEE Transactions on Biomedical Engineering, 55(1), 119-129. (Year: 2007).*

Balasingam, B., Forouzanfar, M., Bolic, M., Dajani, H., Groza, V., & Rajan, S. (May 2011). Arterial blood pressure parameter estimation and tracking using particle filters. In 2011 IEEE International Symposium on Medical Measurements and Applications (pp . 473-476). IEEE. (Year: 2011).*

Forouzanfar, M., Dajani, H. R., Groza, V. Z., Bolic, M., Rajan, S., & Batkin, I. (2015). Oscillometric blood pressure estimation: past, present, and future. IEEE reviews in biomedical engineering, 8, 44-63. (Year: 2015).*

Forouzanfar, M., Balasingam, B., Dajani, H. R., Groza, V. Z., Bolic, M., Rajan, S., & Petriu, E. M. (May 2012). Mathematical modeling and parameter estimation of blood pressure oscillometric waveform. In 2012 IEEE International Symposium on Medical Measurements and Applications Proceedings (pp. 1-6). (Year: 2012).*

Forouzanfar, M., Dajani, H. R., Groza, V. Z., & Bolic, M. (Jun. 2014). Model-based oscillometric blood pressure estimation. In 2014 IEEE International Symposium on Medical Measurements and Applications (MeMeA) (pp. 1-6). IEEE. (Year: 2014).*

Forouzanfar, M., Dajani, H. R., Groza, V. Z., Bolic, M., Rajan, S., & Batkin, I. (2014). Ratio-independent blood pressure estimation by modeling the oscillometric waveform envelope. IEEE Transactions on Instrumentation and Measurement, 63(10), 2501-2503. (Year: 2014).*

Forouzanfar, M. (2014). A modeling approach for coefficient-free oscillometric blood pressure estimation (Doctoral dissertation, Université d'Ottawa/University of Ottawa). (Year: 2014).*

Chen, S., Bolic, M., Groza, V. Z., Dajani, H. R., Batkin, I., & Rajan, S. (May 2010). Improvement of oscillometric blood pressure estimates through suppression of breathing effects. In 2010 IEEE Instrumentation & Measurement Technology Conference Proceedings (pp. 1238-1243). IEEE. (Year: 2010).*

Chen, S., Bolic, M., Groza, V. Z., Dajani, H. R., Batkin, I., & Rajan, S. (2010). Extraction of breathing signal and suppression of its effects in oscillometric blood pressure measurement. IEEE Transactions on Instrumentation and Measurement, 60(5), 1741-1750. (Year: 2010).*

Picone et al., "Accuracy of cuff-measured blood pressure: systematic reviews and metaanalyses." J Am Coll Cardiol. 2017;70(5):572-86.

Wax et al., "Invasive and Concomitant Noninvasive Intraoperative Blood Pressure Monitoring." Anesthesiology: The Journal of the American Society of Anesthesiologists 2011, 115, 973.

Sola et al., "The Handbook of Cuffless Blood Pressure Monitoring, A Practical Guide for Clinicians, Researchers, and Engineers." Springer Nature Switzerland AG 2019.

Tamura, T. "Cuffless Blood Pressure Monitors: Principles, Standards and Approval for Medical Use." IEICE Trans. Commun. 2021, 104, 580-586.

Quan, Xina, "Continuous Non-Invasive Blood Pressure Monitor for Neonates," 1R43HD101175-01 Sbir Phase I, 2020.

Chung, et al., "Binodal, wireless epidermal electronic systems with in-sensor analytics for neonatal intensive care," Science 363, eaau0780 (2019).

Smith et al., "The use of pulse transit time in pediatric sleep studies: A systematic review," j.smrv.2016.11.006.Epub Nov. 30, 2016.

Wippermann et al., "Evaluation of the pulse wave arrival time as a marker for blood pressure changes in critically ill infants and children," J Clin Monit. Sep. 1995;11(5):324-8.

* cited by examiner

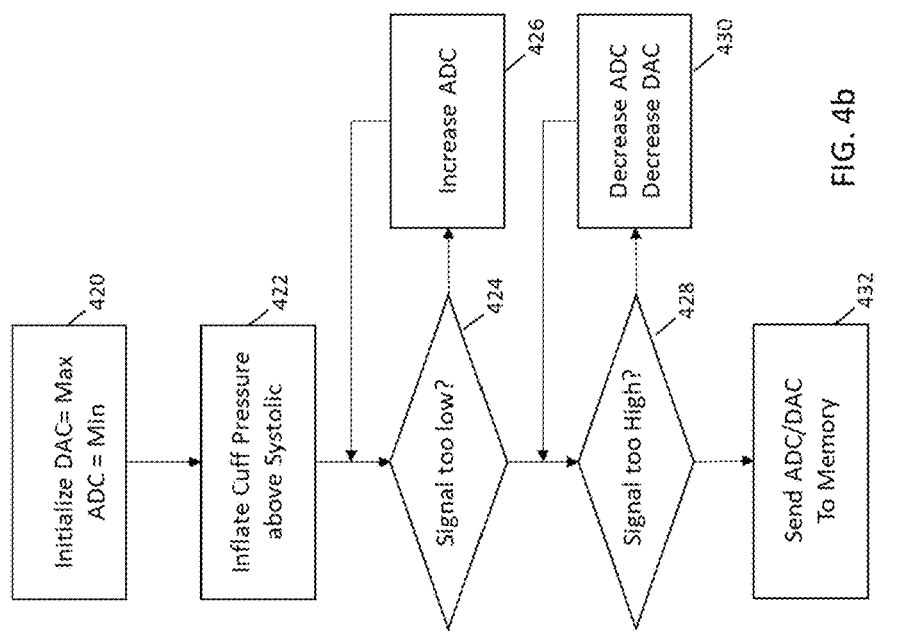
FIG. 4b
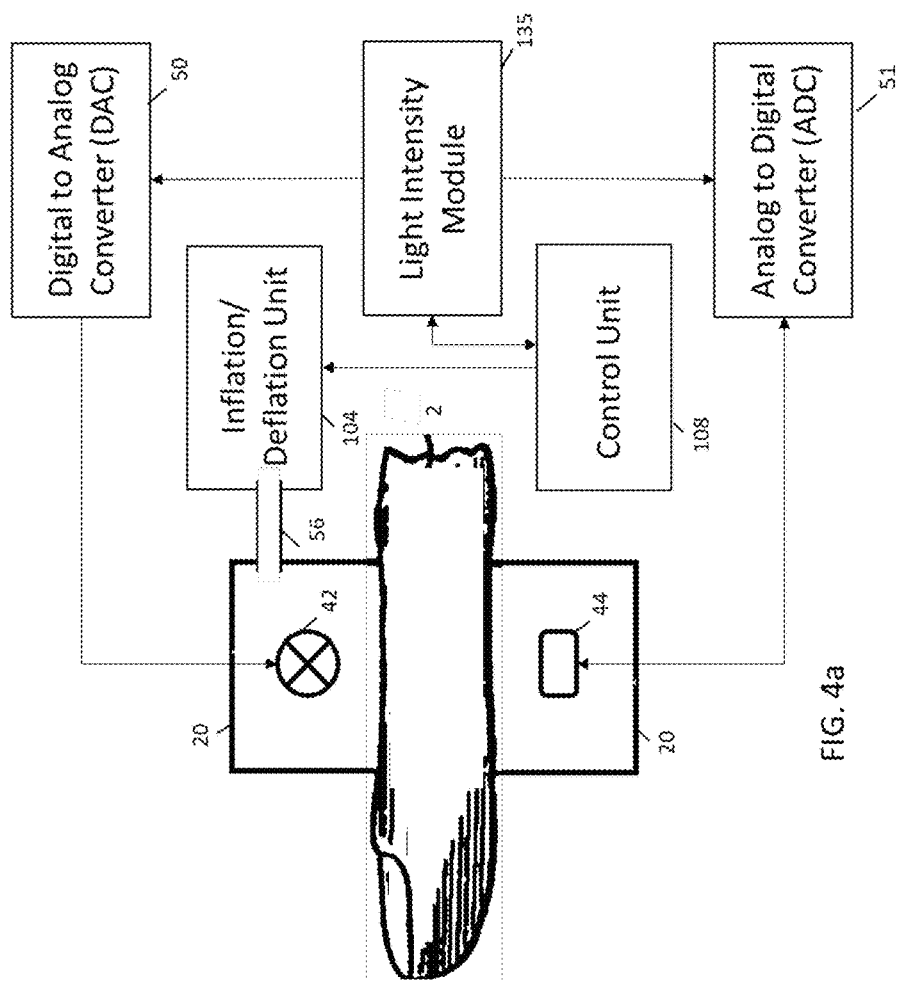
FIG. 4a
FIG. 4

OPTICAL-BASED OSCILLOMETRY BLOOD PRESSURE MEASUREMENT DEVICE

REFERENCES

1. Picone D S, Schultz M G, Otahal P, Aakhus S, Al-Jumaily A M, Black J A, Bos W J, Chambers J B, Chen C H, Cheng H M, Cremer A, Davies J E, Dwyer N, Gould B A, Hughes A D, Lacy P S, Laugesen E, Liang F, Melamed R, Muecke S, Ohte N, Okada S, Omboni S, Ott C, Peng X, Pereira T, Pucci G, Rajani R, Roberts-Thomson P, Rossen N B, Sueta D, Sinha M D, Schmieder R E, Smulyan H, Srikanth V K, Stewart R, Stouffer G A, Takazawa K, Wang J, Westerhof B E, Weber F, Weber T, Williams B, Yamada H, Yamamoto E, Sharman J E. Accuracy of cuff-measured blood pressure: systematic reviews and meta-analyses. J Am Coll Cardiol. 2017; 70 (5): 572-86.
2. Wax, David B., M. D.; Lin, H.-M., Ph.D.; Leibowitz, Andrew B., M. D. Anesthesiology: The Journal of the American Society of Anesthesiologists 2011, 115, 973.
3. Josep Solá·Ricard Delgado-Gonzalo, The Handbook of Cuffless Blood Pressure Monitoring, A Practical Guide for Clinicians, Researchers, and Engineers, Springer Nature Switzerland AG 2019.
4. Tamura, T. Cuffless Blood Pressure Monitors: Principles, Standards and Approval for Medical Use. IEICE Trans. Commun. 2021, 104, 580-586.
5. QUAN, XINA, Continuous Non-Invasive Blood Pressure Monitor for Neonates, 1R43HD101175-01 SBIR Phase I, 2020.
6. Xina Quan et al, PROXIMITY SENSOR CIRCUITS AND RELATED SENSING METHODS, US Publication Number: 20200305740, Oct. 1, 2020.
7. Chung H U, et al., Binodal, wireless epidermal electronic systems with in-sensor analytics for neonatal intensive care, Science 363, eaau0780 (2019).
8. Smith L A, Dawes P J, Galland B C, The use of pulse transit time in pediatric sleep studies: A systematic review, j.smrv.2016.11.006.Epub 2016 Nov. 30.
9. Wippermann C F, Schranz D, Huth R G, Evaluation of the pulse wave arrival time as a marker for blood pressure changes in critically ill infants and children, J Clin Monit. 1995 September; 11 (5): 324-8.
10. Wesseling et al, U.S. Pat. No. 4,539,997, Method and device for controlling the cuff pressure in measuring the blood pressure in a finger by means of photo-electric plethysmograph.
11. Wesseling et al, U.S. Pat. No. 4,529,949, Bias control circuit for light-emitting diode having temperature compensation.
12. Wesseling et al, U.S. Pat. No. 4,510,940, Plethysmograph pressure correcting arrangement.
13. Wesseling et al, U.S. Pat. No. 4,406,289, Device for the indirect, non-invasive and continuous measurement of blood pressure.
14. U.S. Pat. No. 10,285,599, Wearable hemodynamic sensor
15. U.S. Pat. No. 10,098,554, Method and device for continuous, non-invasive determination of blood pressure
16. U.S. Pat. No. 9,974,448, Hemodynamic monitoring
17. U.S. Pat. No. 9,615,756, Device and method for the continuous non-invasive measurement of blood pressure
18. U.S. Pat. No. 8,814,800, Apparatus and method for enhancing and analyzing signals from a continuous non-invasive blood pressure device
19. U.S. Pat. No. 8,798,703, Disposable and detachable sensor for continuous non-invasive arterial blood pressure monitoring
20. U.S. Pat. No. 8,641,632, Method and device for predicting abnormal medical events and/or assisting in diagnosis and/or monitoring, particularly in order to determine depth of anesthesia
21. U.S. Pat. No. 8,343,062, Digital control method for measuring blood pressure
22. U.S. Pat. No. 8,114,025, Device and method for controlling the pressure in an inflatable cuff of a blood pressure manometer
23. U.S. Pat. No. 7,783,345, Impedance-based measuring method for hemodynamic parameters
24. U.S. Pat. No. 7,390,301, Device and method for the continuous non-invasive measurement of blood pressure
25. U.S. Pat. No. 6,669,648, Continuous non-invasive sphygmomanometer

BACKGROUND

Field of the Invention

The present invention is directed to a blood pressure measurement device.

Description of the Related Art

While blood pressure measurement is a staple for the diagnosis of cardiovascular disease, the most popular devices today, brachial cuff oscillometric devices are often inaccurate for patients with hypertension, hypotension, and irregular heartbeat like arterial fibrillation[1,2]. Picone et al. performed a meta-analysis of studies comparing intra-arterial brachial versus cuff-based brachial blood pressure and showed that the latter considerably underestimates systolic blood pressure (by about 6 mmHg) and overestimates diastolic blood pressure (by about 6 mmHg), leading thereby to a large underestimation of pulse pressure by about 12 mmHg[1]. Another meta-analysis of studies by Wax et al found that in the worst cases, the error can be as much as 38 mmHg[2], particularly for patients with hypertension or hypotension, when an accurate measurement is needed the most.

The gold standard of arterial blood pressure measurement is the intra-arterial catheter with the pressure transducer directly touching the blood. In analogy to measure a table length, if the arterial blood pressure is equivalent to the table edge, then the pressure transducer is the ruler.

Since the transducer resides in the intra-arterial catheter directly touching blood, as if the ruler is painted on the table's edge, thus it gives a direct and definitive reading. This is a "direct measurement".

In contrast, oscillometry applies a counter cuff pressure to the artery, which acts as an external ruler. However, since the relationship between the cuff pressure and the arterial pressure is unknown, thus the oscillometric devices "estimate" the arterial blood pressure using data analysis with a set of empirically derived constants. Since these constants do not fit everyone, the measurement error happens, often among these patients who have less representation in statistics.

In recent years, there have been significant efforts in cuffless blood pressure technologies. Most devices combine photo plethysmogram signals with electro-cardiograms (ECG) to derive either pulse arrival time (PAT) or pulse transit time (PTT).[3-4] Another group uses thin-film sensors to measure skin capacitance.[5-6] Without the need to inflate/deflate the cuff, cuffless methods have minimal patient disturbance, seemingly a great technology. However, without the external pressure to use as a "ruler", they must estimate BP by converting their sensor measurements to pressure, which is inherently more difficult than using the same physical quantity of cuff pressure. Unsurprisingly, the tests have shown a significant negative correlation of PTT to systolic pressure.[7-9] Machine learning techniques help cuffless devices guess the pressure range using population-based statistics. However, patients with the highest/lowest BP are often underfitting in the models but overfitting in the test with bigger errors, thus distorting BP estimations to be lower at hypertension but higher at hypotension, for the most vulnerable individuals. To date, most cuffless devices rely on calibration before monitoring a patient, which means to input systolic/diastolic pressures obtained from either A-line or the brachial cuff manually and use a software linear transformation to generate BP readings. The requirement for calibration with external devices renders them unable to address these unmet neonatal critical care unit needs because A-line may be unavailable and the brachial cuff is even more inaccurate in neonates than in adults.

In U.S. Pat. No. 4,539,997, Wesseling et al added a photo plethysmogram sensor to a finger-mounted air cuff, in addition to the inflation/deflation system and pressure sensor in the traditional oscillometric device. They related the photo plethysmogram to the artery volume and identified that if the photo plethysmogram is controlled at an artery unload point where the transmural pressure defined as the arterial pressure minus the cuff pressure is zero, then the external cuff pressure equals the internal arterial pressure, and can be measured continuously. Here photo plethysmogram acts as an "eye" to align the table edge with the ruler in the table measurement analogy, thus this system provides an "indirect measurement", and has the potential to be accurate. However, each patient has a unique relationship function of photo plethysmogram and pressure. Without a systematic hardware and software approach to obtain and utilize this relationship, their system is still not accurate and even worse than the oscillometric devices. This is as if the "eye" doesn't have the knowledge of how to view the ruler perpendicularly, so the reading is still incorrect.

SUMMARY

To solve the inaccuracy problem, the present invention describes an accurate optical-based oscillometric blood pressure (OBOBP) measurement device, which builds an individualized relationship of artery volume and pressure for each subject, thus can measure the arterial blood pressure accurately. In the table measurement analogy, it has not only both the ruler and the eye but also the knowledge to view the ruler perpendicularly, to make a true "indirect measurement" of blood pressure.

In one or more embodiments of the present invention, an accurate optical-based oscillometric blood pressure measurement device comprises a cuff that compresses an artery of a blood pressure measurement site, an inflation/deflation unit that increases and decreases pressure inside the cuff, a pressure detection unit that detects a cuff pressure, a volume detection unit that detects an arterial volume signal indicating a volume of the artery per unit length, and a control unit that controls the pressure of the cuff by controlling the inflation/deflation unit using the artery volume signal, and an extraction unit that extracts the relationship of the arterial volume with the transmural pressure defined as the difference between arterial pressure and cuff pressure, and then the systolic, diastolic, and mean arterial pressures, and heart rate for each heartbeat.

In one or more embodiments of the present invention, a volume detection unit is provided that takes the plethysmogram sensed from one or more photodiodes as the input and converted it into the arterial volume as the optical oscillometrygram. It adjusts the gains or the digital to analog converters (DAC) for the light emission diode driver circuit, also adjusts the gains or the analog to digital converters (ADC) for the photodiode driver circuit, to achieve the maximum signal to noise ratio.

In one or more embodiments of the present invention, a control unit is provided that dynamically calculates the inflation/deflation slopes and the start/stop pressures during the operation. With an advanced feedback servo design for the pressure control unit, it accurately traces the prescribed controller set point.

In one or more embodiments of the present invention, an extraction unit is provided that relates the inflation/deflation pressures with optical oscillometrygram, to derive the pressure and volume functions. Therefore, it can further identify the points where the transmural pressure is zero and determine the systolic, and diastolic pressures. In addition, combining the information of systolic and diastolic volume changes, it calculates the mean arterial pressures. Finally, it computes the volume point where the artery is unloaded.

The optical-based oscillometric blood pressure measurement device is thus able to obtain the blood pressures of a subject with high accuracy.

BRIEF DESCRIPTION OF THE DRAWINGS

FIG. 4 consists of two diagrams describing the operation of the light intensity adjustment to achieve a better signal to noise ratio, where FIG. 4a illustrates the hardware components and FIG. 4b shows the algorithm, according to one or more embodiments of the present invention.

DETAILED DESCRIPTION

Figure 1:
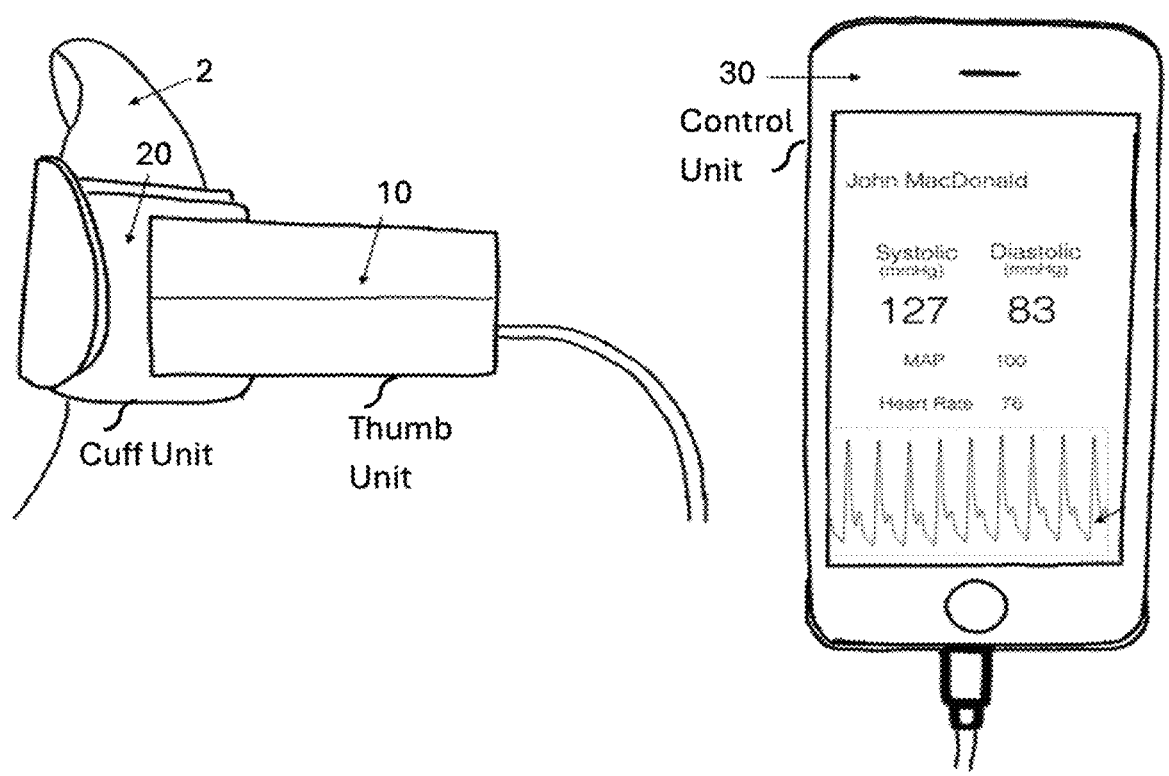
FIG. 1 is an external perspective view of a continuous blood pressure measurement device, according to one or more embodiments of the present invention.

FIG. 1 is an external perspective view of the optical-based oscillometric blood pressure measurement device 1, according to an embodiment of the present invention. Referring to FIG. 1, the blood pressure measurement device 1 is provided with a main body 10, a cuff 20, and an operation unit 30. The cuff 20 can be wrapped around the measurement site 2 of a subject. The main body 10 is attached to the cuff 20. An operation unit 30 is for receiving instructions from a user, and display the measurements include the systolic, diastolic, mean arterial pressures, and heart rate of the subject.

In the present embodiment, "the measurement site of a subject" denotes the body parts of a subject that cuff 20 is applicable, including but not limited to, the upper arm, forearm, wrist, finger, and ankle. In the following description, the cuff 20 is fitted on the thumb of the subject.

Note that while a configuration in which the main body 10 of the blood pressure measurement device 1 in the present embodiment is attached to Cuff 20, as shown in FIG. 1, is described as an example, an embodiment is possible in which the main body 10 and the cuff 20 are connected by an air tube (air tube 56 in FIG. 2 mentioned below), such as employed with a wrist mount monitor. Also, the main body 20 and the operation unit 30 can be combined into one unit as an alternative embodiment.

Figure 2:
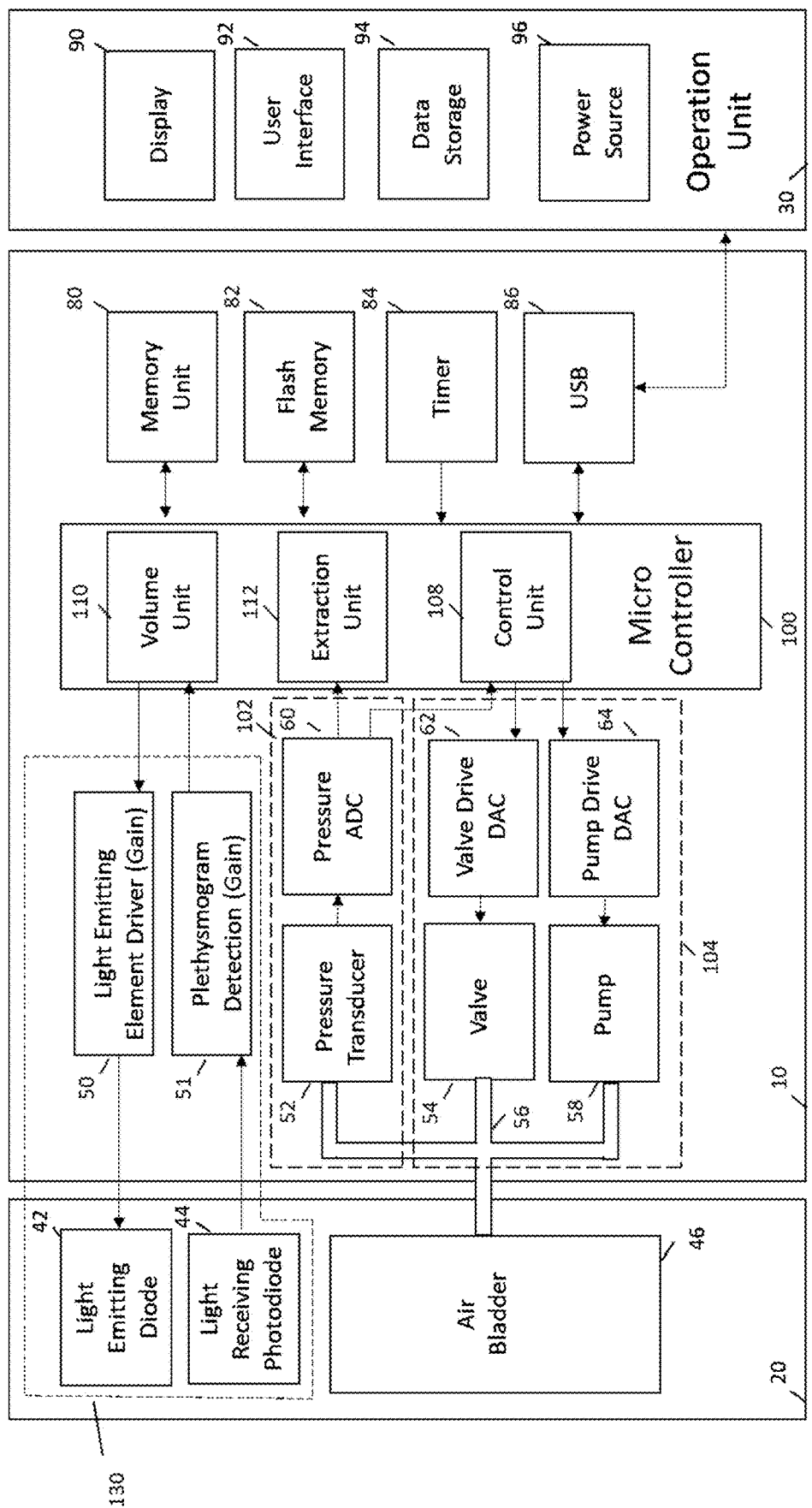
FIG. 2 is a block diagram showing a hardware configuration of the optical-based oscillometric blood pressure measurement device 1, according to one or more embodiments of the present invention.

FIG. 2 is a block diagram showing a hardware configuration of the optical-based oscillometric blood pressure measurement device 1, according to one or more embodiments of the present invention. Referring to FIG. 2, Cuff 20 of the optical-based oscillometry blood pressure measurement 1 includes the airbag 46 and a plethysmogram sensor module 130, which is constituted by the light-emitting diode (LED) 42 and the light-receiving photodiode 44. The LED 42 irradiates light toward an artery, and the light-receiving photodiode 44 receives light irradiated by the LED 42 that has been transmitted or reflected by the artery. It should be pointed out that the LED 42 and the photodiode 44 can be plural numbers, and their numbers of elements may be unequal.

Referring to FIG. 2, the main body 10 includes a microcontroller unit (MC) 100 for performing centralized control of the various units and performing various arithmetic processing, a memory unit 80 for storing programs for causing the MC 100 to perform prescribed operations and various data, nonvolatile memory for storing the boot loader and measured blood pressure data, such as flash memory 82, a timer 84 that clocks the current time and outputs time data to the MC 100, and a USB 86 connection to the operation unit 30, to receive the user commands, send out the data stream, and get the power supplying. The MC 100 further comprises computational units including the volume unit 110, the extraction unit 112, and control unit 108. They will be described in detail in the later sections.

The main body 10 further includes the cuff pressure detection unit 102 consisting of a pressure transducer and its analog to digital converter (ADC), and the inflation/deflation system 104 includes a pump and valve with their driver circuitries. The pump 58 supplies air to the airbag 46 via air tube 56, in order to increase the cuff pressure. Valve 54 is opened or closed in order to discharge air from airbag 46 via air tube 56 or enclose air in airbag 46. The pump drive circuit 64 controls the drive of the pump 58 by the control unit 108. The valve drives circuit 62 controls the opening and closing of valve 54 by the control unit 108. The light-emitting diode drives circuit 50 controls the amount of light emission of the light-emitting diode 42, according to a command signal from the volume unit 110. Plethysmogram detection gain or ADC 51 can amplify the amount of transmitted or reflected light in the absorption band of hemoglobin included in the blood (red blood cells) flowing through the blood vessels that reach the photodiode 44 by adjusting its gain 51 by the volume unit 110. In one preferred embodiment, the light-emitting diode driver 50 and plethysmogram detection circuit 51 can be packaged as one analog front end (AFE) circuitry. In other embodiments, they can be separated circuitries Referring to FIG. 2, the operation unit 30 has a display unit 90 to show the monitoring result, and user interface unit 92 to take user's command to turn on/off the device and operate in various modes, a data storage unit 94 to save monitoring data, and a power source 96 to supply power for the optical-based oscillometric blood pressure measurement device 1.

Figure 3:
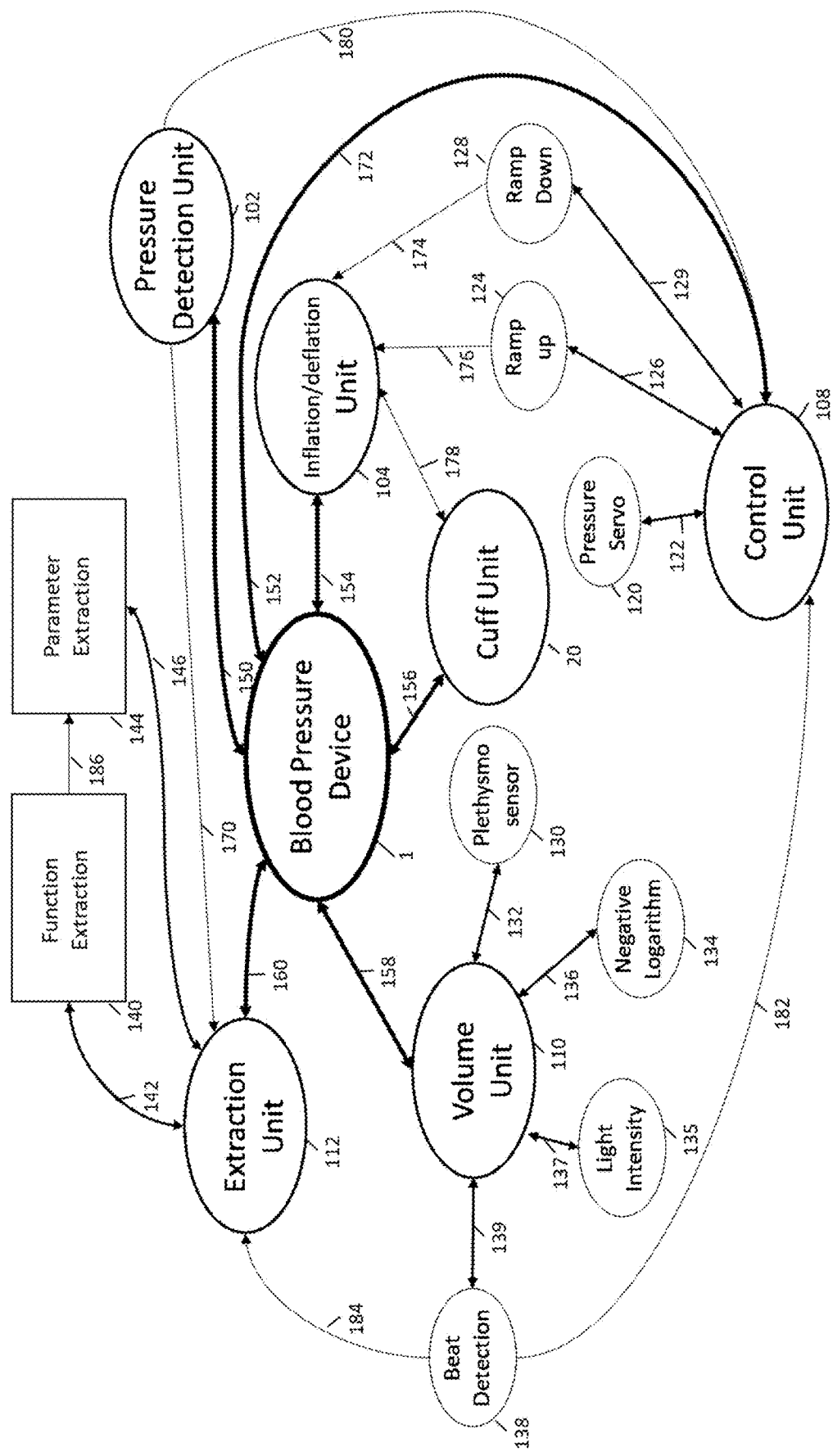
FIG. 3 is a block diagram illustrating the functional operation of the optical-based oscillometric blood pressure measurement device 1, according to one or more embodiments of the present invention.

FIG. 3 is a block diagram illustrating functional operation of the optical-based oscillometry blood pressure measurement device 1, according to one or more embodiments of the present invention. As shown in FIG. 3, the blood pressure measurement device 1 may include a finger cuff unit 20 wrapping around to a subject's measurement site 2 that maybe finger, wrist, arm, or ankle, an inflation/deflation unit 104 that supplies proper air pressure to the cuff airbag 46, a pressure detection unit 102 that measures the air pressure inside the cuff airbag 46, a control unit that commands the inflation/deflation unit 104 to generate a desired pressure value inside the cuff air bag 46, a volume unit 110 that measures the artery volume, and an extraction unit 112, which generates the system outputs. Bold double arrows 150, 152, 154, 156, 158, and 160 connect the blood pressure device 1 to its component units.

Referring to FIG. 3, the control unit further includes a pressure servo module 120, a ramp-up module 124, and a ramp-down module 128. The ramp-up/ramp-down modules 120 and 128 set up the speed and limit for inflation and deflation, and the pressure servo 124 ensures the realization of the speed and limit using a feedback controller. Double arrows 122, 126, and 129 connect the control unit 108 to its component modules.

Referring to FIG. 3, the volume unit further includes photoplethysmogram sensor module 130 to acquire photoplethysmogram, a negative logarithm module 134 to convert photoplethysmogram into the volume of a blood vessel per unit length, a light intensity module 137 to adjust photodiode circuitry to enhance the signal, and a beat detection unit 138 to identify systolic/diastolic/heart rate in volume data. Double arrows 132, 136, 137, and 139 connect the volume unit 110 to its component modules.

Referring to FIG. 3, the extraction unit further includes a function extraction module 140 that generates the pressure and volume relationship, and a parameter extraction module 144 that extracts systolic, diastolic, mean arterial pressure. Double arrows 142 and 144 connect the extraction unit 112 to its component modules.

Referring to FIG. 3, the operations of the optical-based oscillometric blood pressure measurement device 1 are described in more detail. The pressure detection unit 102 and the volume unit 110 are constantly sensing the blood measurement site 2. Using the signals from the pressure detection unit 102 and the beat detection module 138 in the volume unit 110, the ramp-up/ramp-down modules 126 and 129 in the control unit 108 invoke the pressure servo 120 to command the inflation/deflation unit 102 respectively. At the end of deflation, the extraction unit 112 takes the cuff pressure from the pressure detection unit 102 and the volume waveform with the systolic/diastolic points generated by the beat detection module 138, to invoke the function extraction module 140 to extract the pressure/volume relationship. Using this relationship, the parameter extraction module 144 further derives the blood pressure parameters. Both the pressure/volume relationship and the blood pressure parameters are the output of the blood pressure measurement device 1. Here arrows 170, 174, 176, 178, 180, 182, 184, and 186 indicate the signal links.

FIG. 4 consists of two diagrams describing the adjustment of circuitries to obtain the photoplethysmogram that has the maximum signal to noise ratio (SNR) in the light intensity module 135, according to one or more embodiments of the present invention. Referring to FIG. 4, FIG. 4a is a chart showing the principle of operation, where 42 is the light-emitting diode, and 44 is the photodiode. They are connected to their driver circuitries 50 and 51 respectively, which are controlled by the light intensity module 135. Since both the LED 42 and the photodiode 44 reside inside the cuff unit 20, their interactions with cuff pressure are affected by the inflation/deflation unit 104 and control unit 108.

FIG. 4a illustrates a preferred embodiment where the photodiode 44 measures the transmission light from LED 42 is located on the opposite side of the artery at the measurement site 2. Another embodiment is that the LED 42 located on the same side of the artery at measurement site 2 as the photodiode 44, measuring the refection light.

Referring to FIG. 4, FIG. 4b is a flowchart describing the light intensity adjustment process. Initially, before the cuff inflation, the DAC 50 is set to the maximum value for the maximum light and ADC 51 the minimum for the minimum noise, by step 420. After the cuff pressure reaches above the subject systolic at 422, the pressure is held steady and the adjustment process starts. The reason why the adjustment happens at this pressure is that the photoplethysmogram and the cuff pressure are correlated, thus both low SNR and signal saturation need to be avoided. The first test is to check if the signal is too low at 424 and increase ADC 51 at 426 recursively until the condition 424 is met. Similarly, condition 428 is tested and adjusted by 430. Then finally a satisfying set of ADC 50 and DAC 51 values are stored to memory 80 for the subject.

Figure 5:
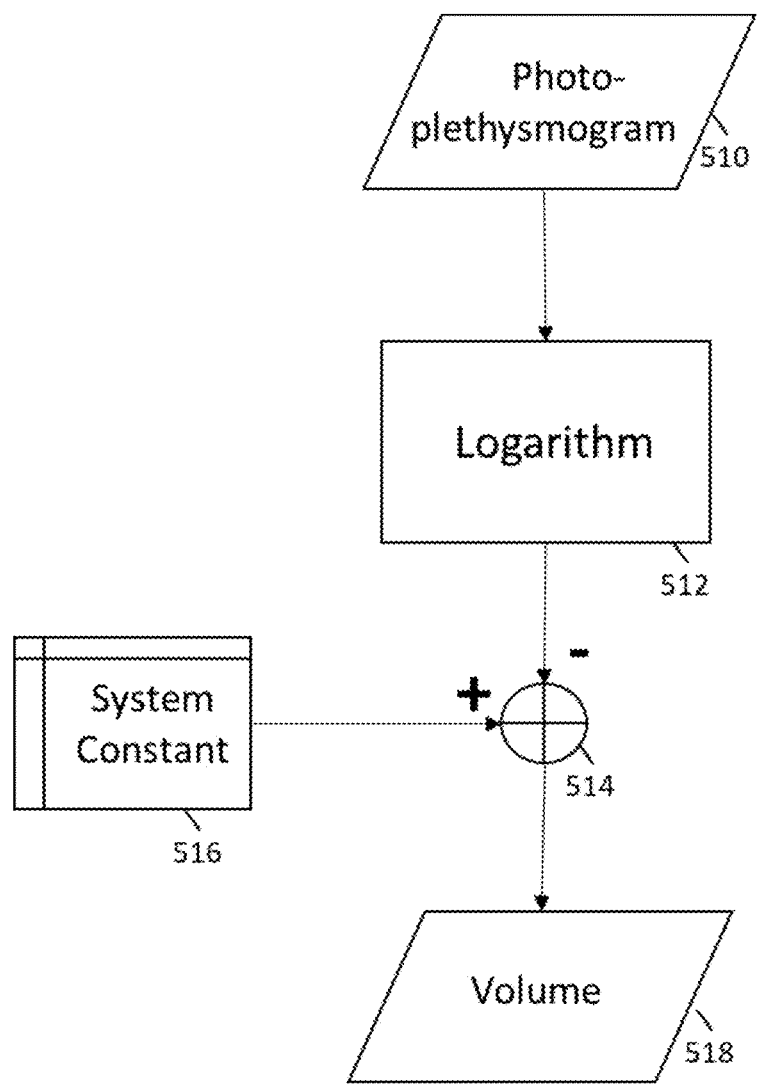
FIG. 5 is a flowchart describing the conversion process from the photoplethysmogram to the artery volume, according to one or more embodiments of the present invention.

FIG. 5 is a flowchart describing the conversion process from the photoplethysmogram to the artery volume in the negative logarithm module 134, according to one or more embodiments of the present invention. Referring to FIG. 5, the input to the module is the photoplethysmogram 510. The system constant 516 represents the equivalent volume when the artery is completely empty, which is obtained by emitting an LED to photodiode in a light sealed compartment and then taking the logarithm of the photoplethysmogram under this condition. The input photoplethysmogram 510 is transformed by logarithm and subtracted from the system constant 516, which results in the artery volume 518, represented by the artery cross-section area per unit length.

FIG. 6 is a state machine diagram with function flow charts describing heart beat detection process using the volume waveform, according to one or more embodiments of the present invention. Referring to FIG. 6, FIG. 6a further illustrates a volume waveform that contains two heartbeats. The goal of beat detection module 138 is to identify the parameters Dia_tmr, Sys_tmr, Over_tmr, the maximum of Sys_vol, and the minimum of Dia_vol, as marked in FIG. 6a.

Figure 6A:
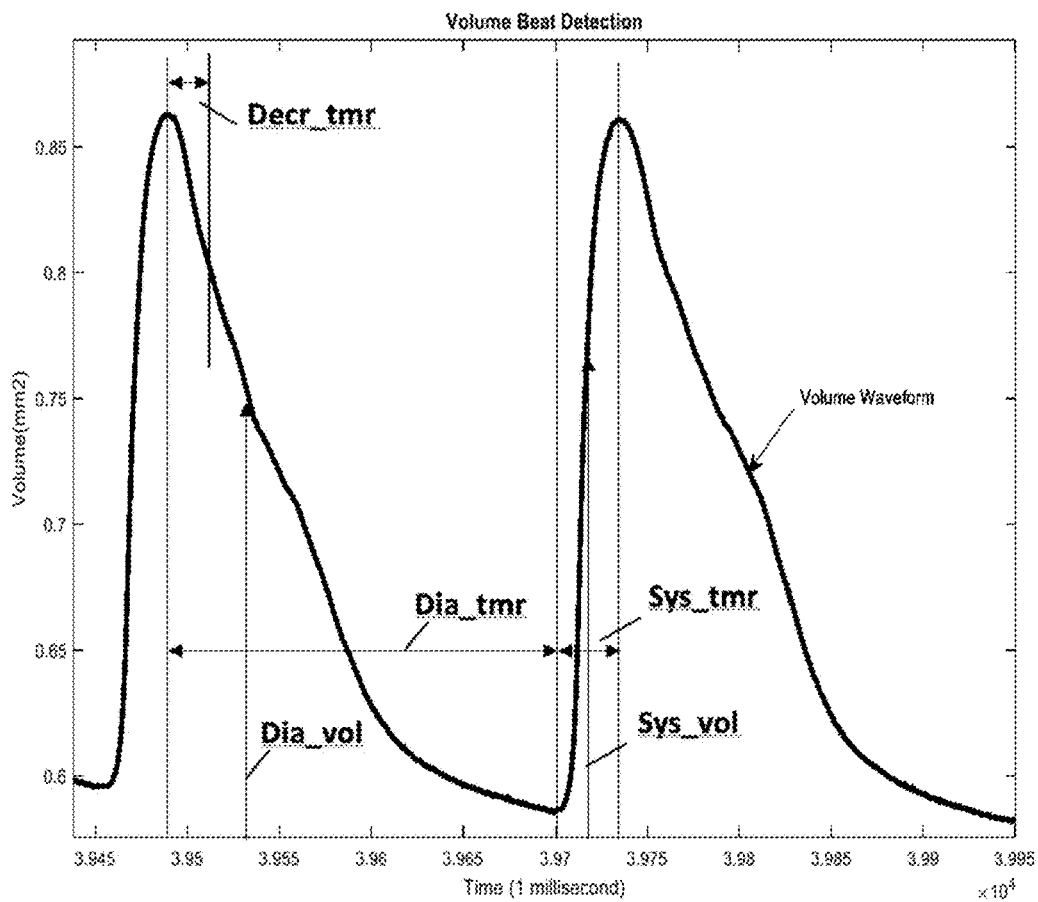
FIG. 6a illustrates the input signal, FIG. 6b draws the operating states, FIG. 6c and FIG. 6d describe the algorithms for up-trend and down-trend respectively, according to one or more embodiments of the present invention.
Figure 6B:
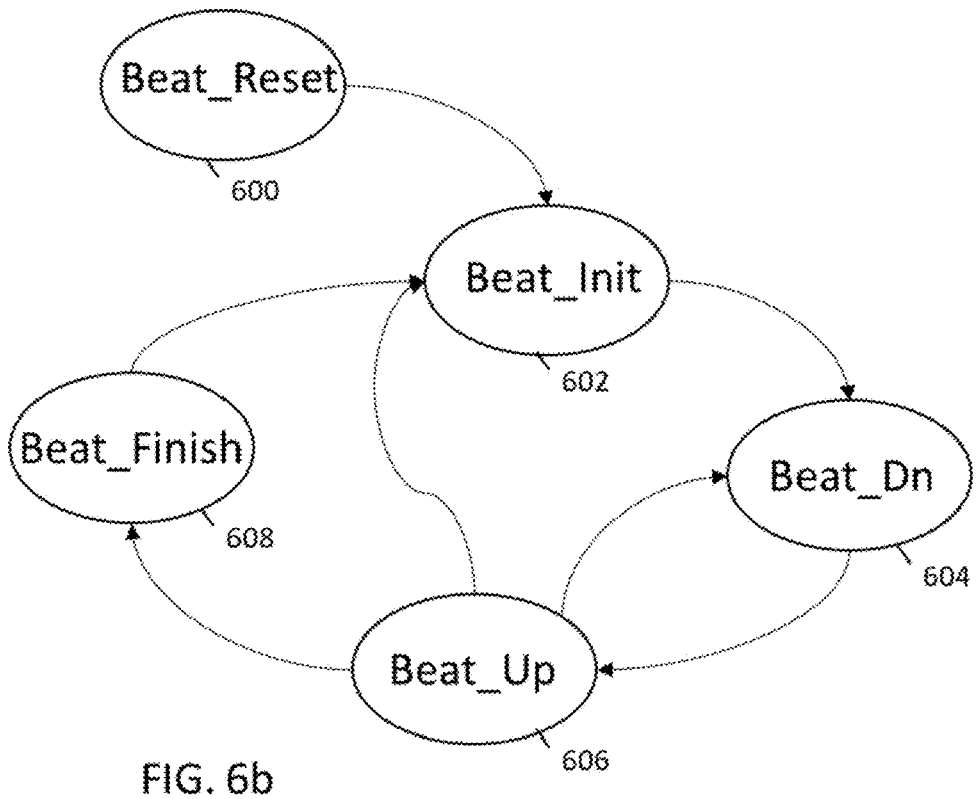
FIG. 6 is a state machine diagram with function flow charts describing the heartbeat detection process using the volume waveform, where

Referring to FIG. 6, FIG. 6b further shows 5 states including Beat_Reset 600, Beat_Init 602, Beat_Dn 604, Beat_Up 606, and Beat_Finish 608. Of the 5 states, Function in Beat Reset sets the operational parameters, function in Beat_Init sets subject-specific parameters, and function in Beat_Finish outputs the systolic/diastolic/heart rate information. Bear_Dn and Beat_Up state functions are further described as the following.

Figure 6C:
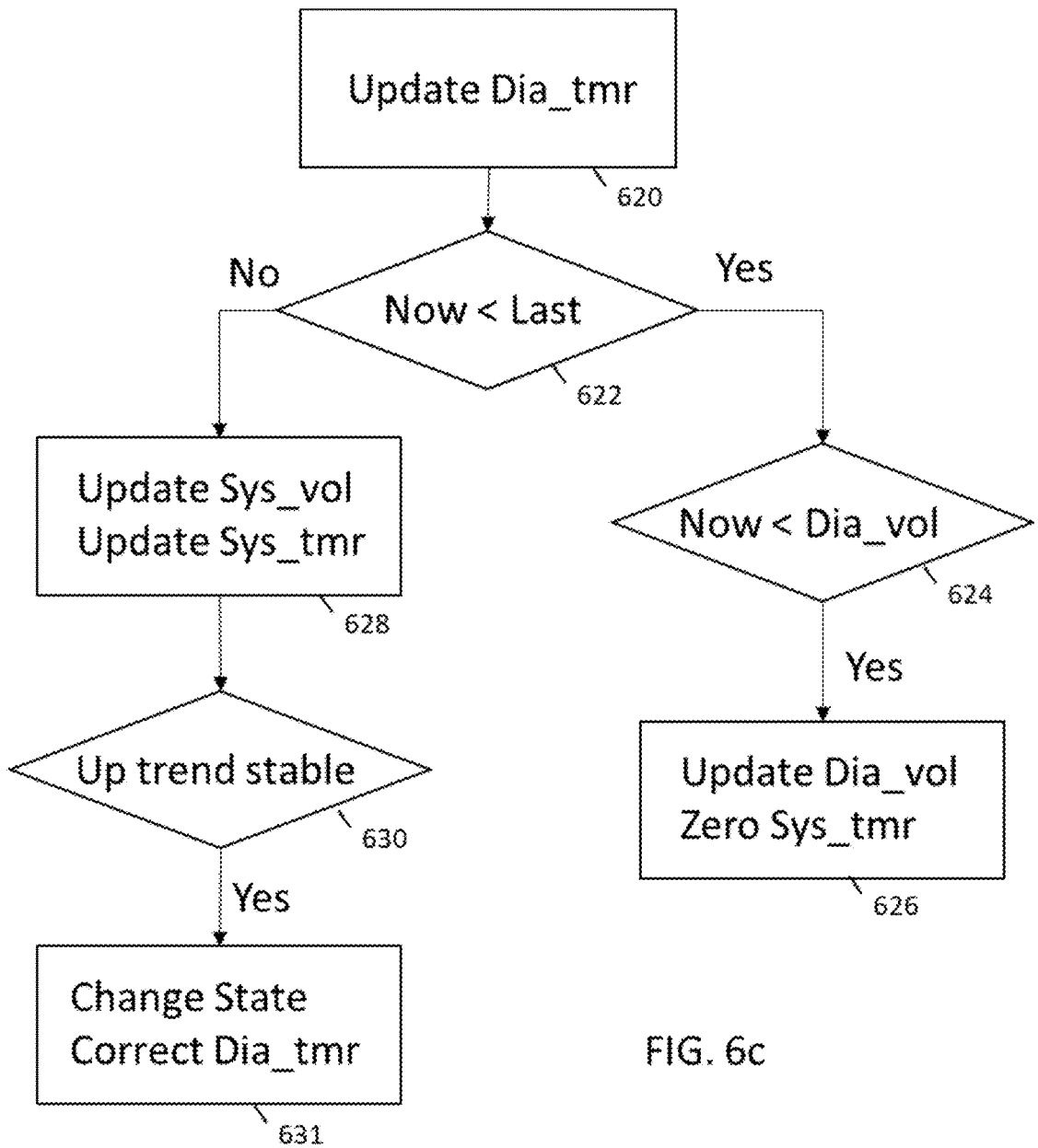

Referring to FIG. 6, FIG. 6c is a flowchart that describes the function in the state Beat_Dn, which represents the diastolic phase. Here "Now" is the input of a new volume data point. First, the diastolic phase timer Dia_tmr is updated in 620. If the current volume is less than the Last, the previous volume in 622, then it will further be compared to the Dia_Vol, the smallest volume during the heartbeat, and update parameters in 626 if the condition 624 is met. If the condition in 622 is not met, then systolic parameters are updated in 628, and then the condition in 630 is tested to ensure the upward trend is stable. If the condition is met, then the state is changed to Beat_Up, and Dia_tmr are corrected by subtracting Sys_tmr, both are done in 631.

Figure 6D:
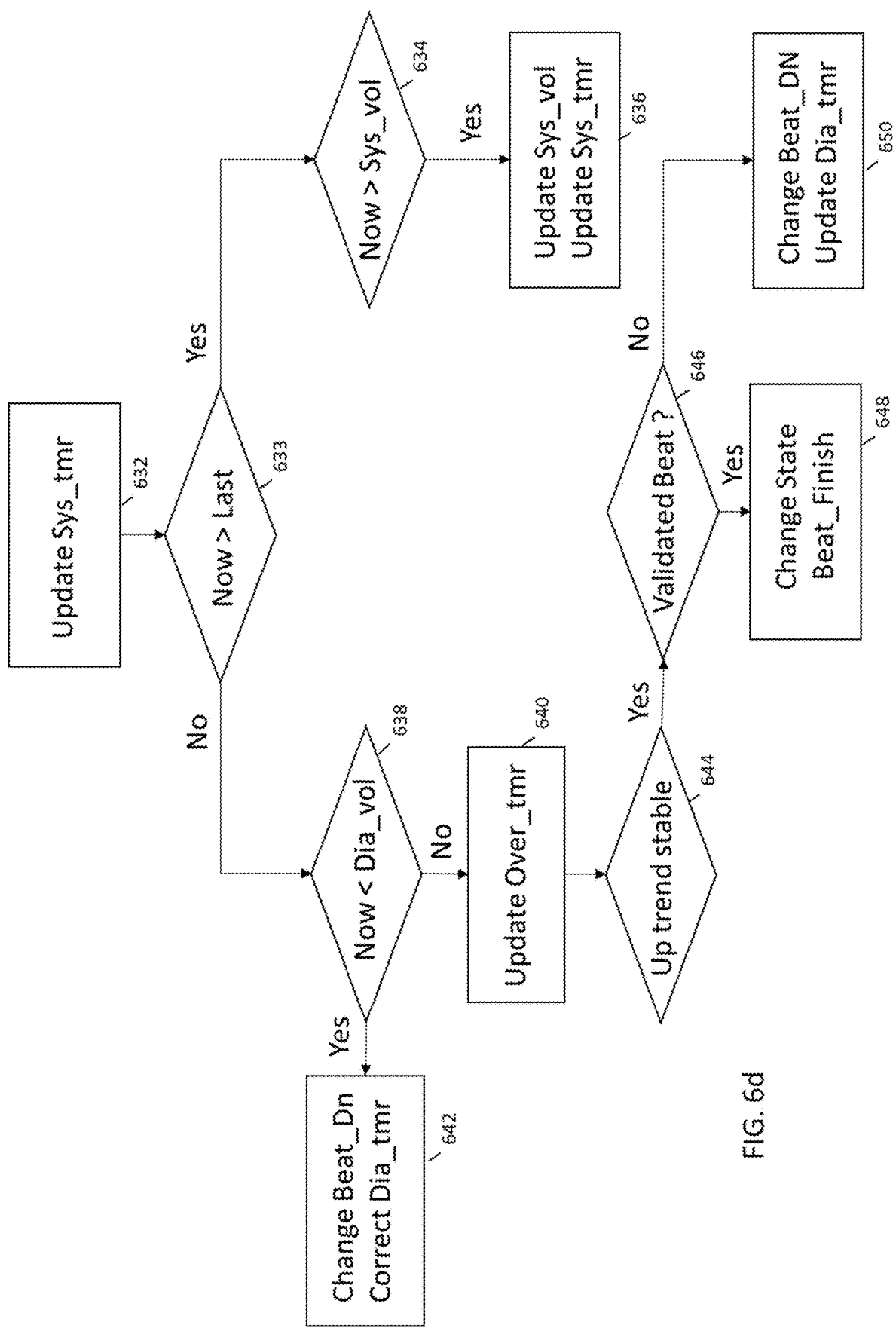

Referring to FIG. 6, FIG. 6d is a flowchart that describes the function in the state Beat_Up, which represents the systolic phase. Here "Now" is the input of a new volume data point. First, the systolic phase timer Sys_tmr is updated in 632. If the current volume is more than the Last, the previous volume in 633, then it will further be compared to the Sys_Vol, the biggest volume during the heartbeat, and update parameters in 636 if the condition 634 is met. If the condition in 633 is not met, then the condition in 638 is further checked. If it is true, then the state is changed back to Beat_Dn, and Dia_tmr has corrected accordingly. If not, Over_tmr is updated in 640, and the Uptrend is tested in 644. If the condition is met, the beat is validated using both time and magnitude criteria in 646. If the condition is satisfied, the state is changed to Beat_Finish in 648, otherwise, the state is changed to Beat_Dn, and Dia_tmr is updated in 650.

Figure 7A:
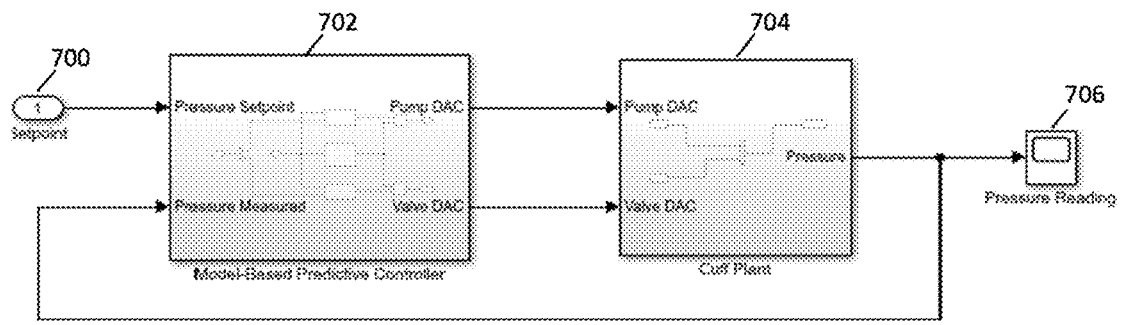
FIG. 7a is an overview and FIG. 7b gives details of the controller, according to one or more embodiments of the present invention.

FIG. 7 consists of two diagrams describing the pressure servo 120 in the control unit 108 that is used to obtain the desired inflation/deflation in the cuff airbag 46, according to one or more embodiments of the present invention. Referring to FIG. 7, FIG. 7a is a diagram showing an overview of the pressure servo. The input of the system is the pressure setpoint 700, and the model-based predictive controller (MPC) 702 computes the pump PWM and valve DAC and sets them in their circuitries respectively. The cuff plant 704 then acts accordingly, and the pressure sensed by the pressure detection unit 102 feedback the pressure to MPC 702.

Figure 7B:
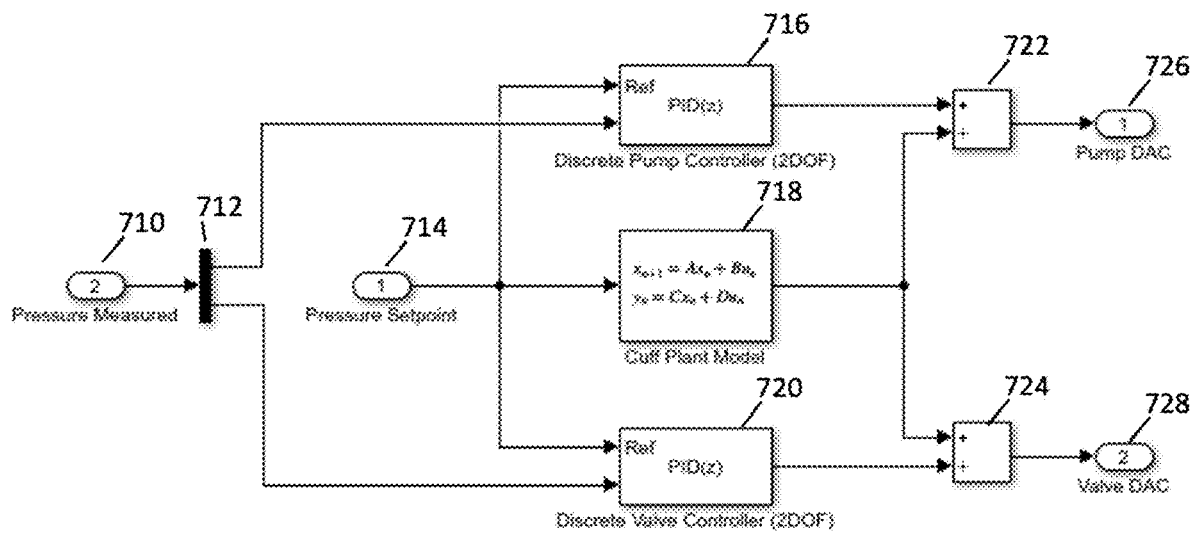
FIG. 7 consists of two diagrams describing the operation of the pressure servo, where

Referring to FIG. 7, FIG. 7b is a diagram showing the details of MPC 702. The inputs of the system include the pressure setpoint 714 and the pressure measured 710. The pressure measured 710 goes into a signal splitter 712, then routed to the pump and valve controllers 716 and 720 respectively. Meantime, the pressure setpoint 714 is routed to 716 and 720 also, which are the discrete-time PID controllers with 2 degrees of freedom shown in the following equation:

$$P(b \cdot r - y) + I \cdot T_s \frac{1}{z-1}(r-y) + D \frac{N}{1 + N \cdot T_s \frac{1}{z-1}}(c \cdot r - y)$$

Where r is the pressure setpoint, y the measured pressure, P, I, and D is the proportional, integral, and derivative coefficients, $T_s$ is the sampling time, N is the filter coefficient for the derivative, and b and c are the weights for the set point. With advanced features such as setpoint weighting, anti-windup, external reset, and signal tracking, the controller can be tuned accurately for the target plant 704. The cuff plant model 718 can be obtained using any system identification method familiar to these skilled in the field. The general form of the 718 can be written as $$G_i = f(r, G_{i-1}), \text{ and } G = \{PWM, DAC\}.$$

At the run time, the model 718 can generate desired pump PWM and DAC and then add together with the output from the PID controllers 716 and 720 by adders 722 and 724 and output the final pump PWM 726 and valve DAC 728.

In a preferred embodiment, the pump is a piezoelectric pump that allows backward leakage of pneumatic pressure out of the pump. Thus, the control strategy is to minimize the pump power usage to set the valve to the minimum leakage state in model 718.

Figure 8:
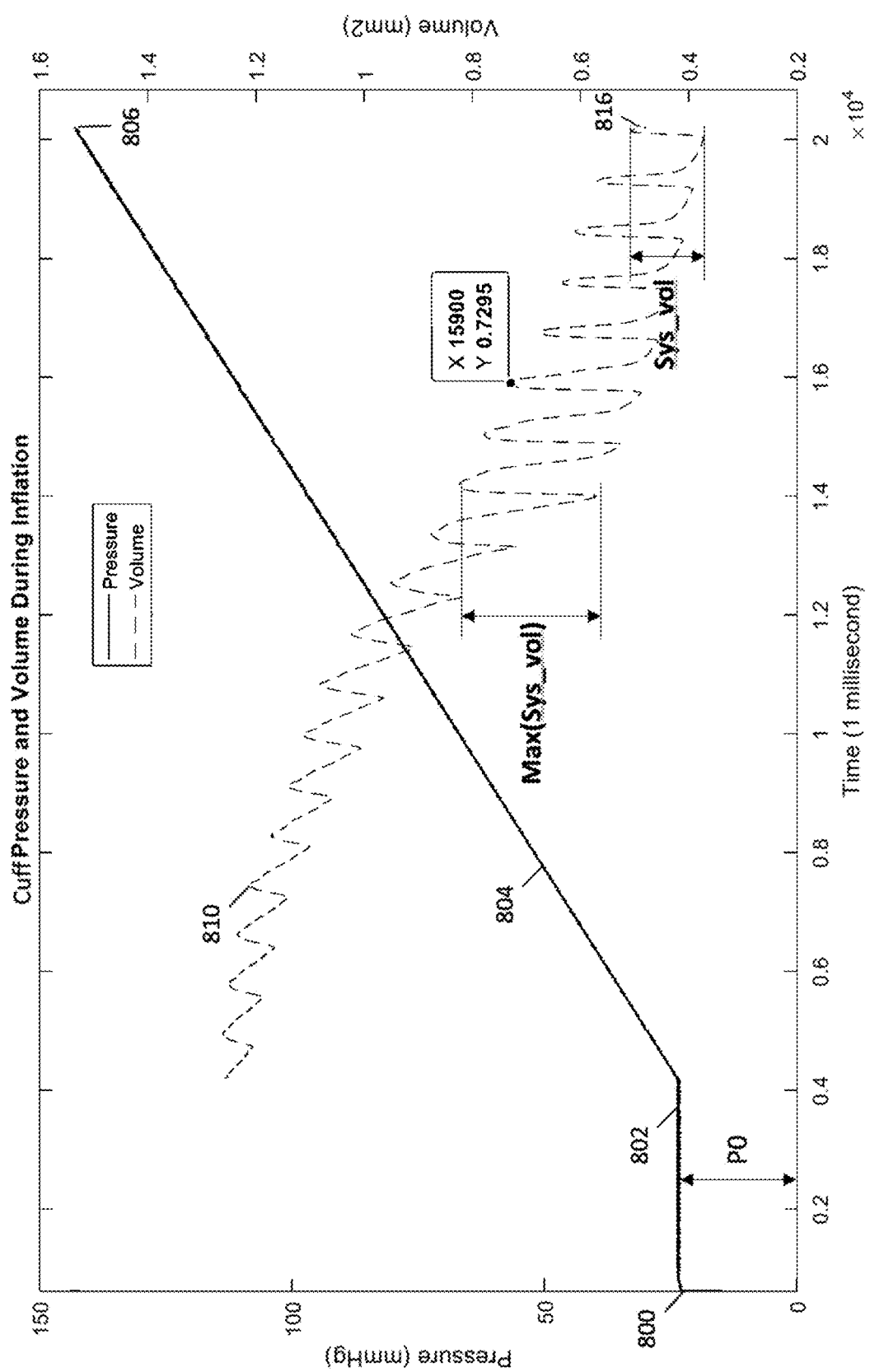
FIG. 8 is a pressure and volume chart describing the inflation control process, according to one or more embodiments of the present invention.

FIG. 8 is a pressure and volume chart describing the inflation control process, according to one or more embodiments of the present invention. Referring to FIG. 8, the pressure is marked by the starting point 800, flat phase 802, ramp up phase 804, and stop point 806. During the inflation, the corresponding artery volume 810 is a waveform, where the endpoint 816 is preceding the pressure stop point 806 in time. At the starting point, the cuff pressure is set to P0, a pressure that squeezes the measurement site 2 to eliminate the signal influence caused by capillaries and other soft tissues. In the flat phase 802, the number of heartbeats is identified, and the average sampling time T per heartbeat is identified. Then the slope of the ramp-up phase 804 can be calculated as Slope=100 (mmHg)/$(ns \times T)$ Here ns is for the number of heartbeats per 100 mmHg. While ns can be a preset constant, or a function of the subject's age, sex, height, and body mass index (BMI).

The pressure end point 806 is determined by observing the peak height of the volume waveform. When a heartbeat is identified as shown in FIG. 7, its Sys_vol is compared to the maximum of all Sys_vol. If the following condition met, Sys_vol<$cs$×max(Sys_vol); $cs$—system constant then the inflation is ended. During inflation, the diastolic pressure pd can be calculated accurately and will be described in the later sections in detail.

Figure 9:
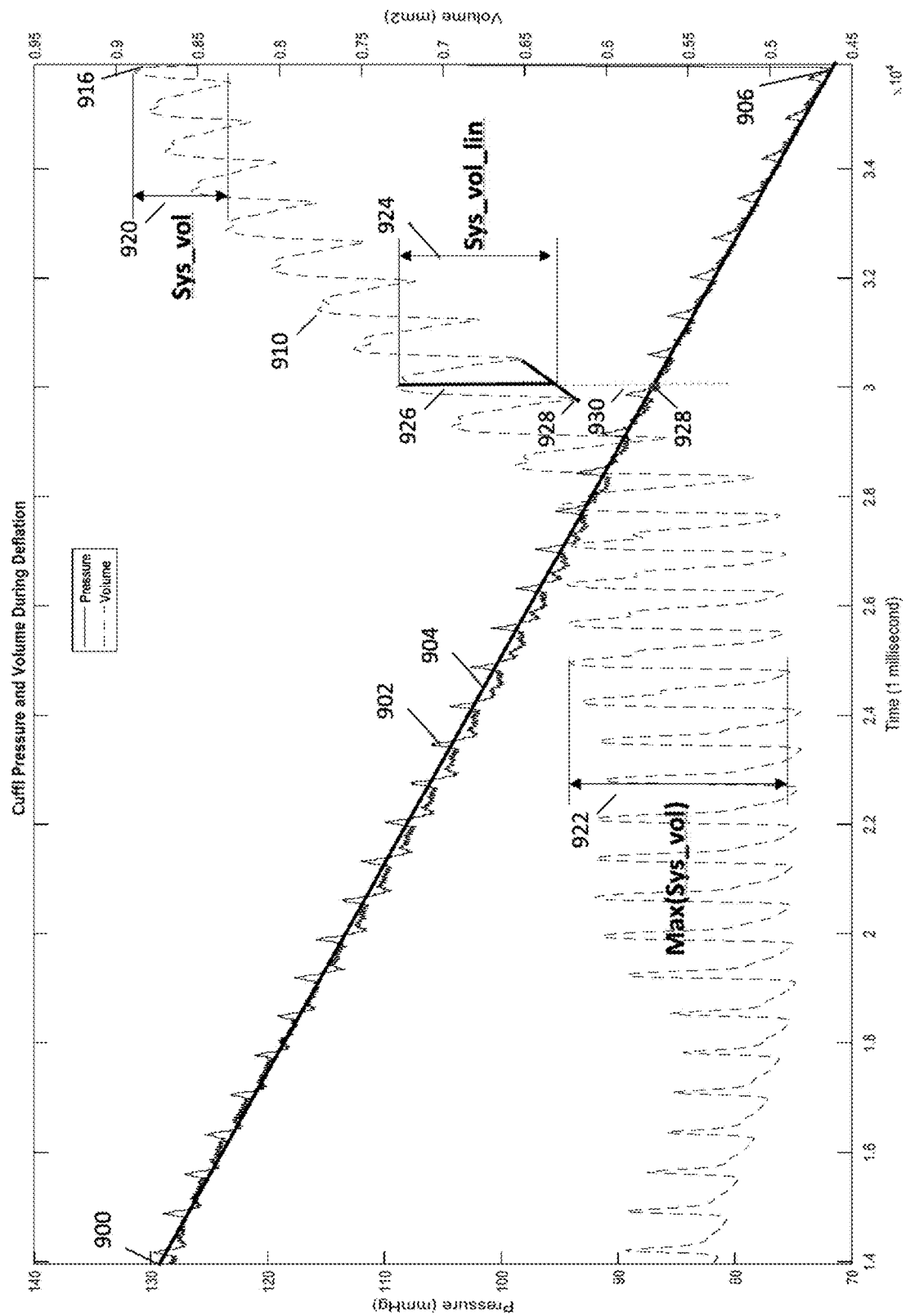
FIG. 9 is a pressure and volume chart describing the deflation control process, according to one or more embodiments of the present invention.

FIG. 9 is a pressure and volume chart describing the deflation control process, according to one or more embodiments of the present invention. Referring to FIG. 9, the pressure is marked by the actual pressure waveform 902, and its command pressure line 904. In the context of deflation control, the actual waveform 902 and its command-line pressure 904 can be used exchangeable without affecting the operation. The deflation starting point 900, and the deflation stop point 906. During the deflation, the corresponding artery volume 910 is a waveform, where the endpoint 916 is preceding the pressure stop point 906 in time. At the starting point, the cuff pressure is equal to the pressure at the end of the inflation phase. Then the slope of the deflation phase 904 can be calculated as Slope=$(pi-pd)$ (mmHg)/$(nd*T)$ Here pi is the pressure at the end of inflation, pd is the diastolic pressure, and nd is for the desired number of heartbeats in the pressure range from the end of inflation to the diastolic pressure. While nd can be a preset constant, or a function of the subject's age, sex, height, and body mass index (BMI).

The pressure endpoint 906 is determined by observing the peak height of the volume waveform. When a heartbeat is identified as shown in FIG. 7, its Sys_vol is compared to the maximum of all Sys_vol. If the following condition met, Sys_vol<$cd$*max(Sys_vol); $cd$—system constant then the deflation is ended.

Figure 10:
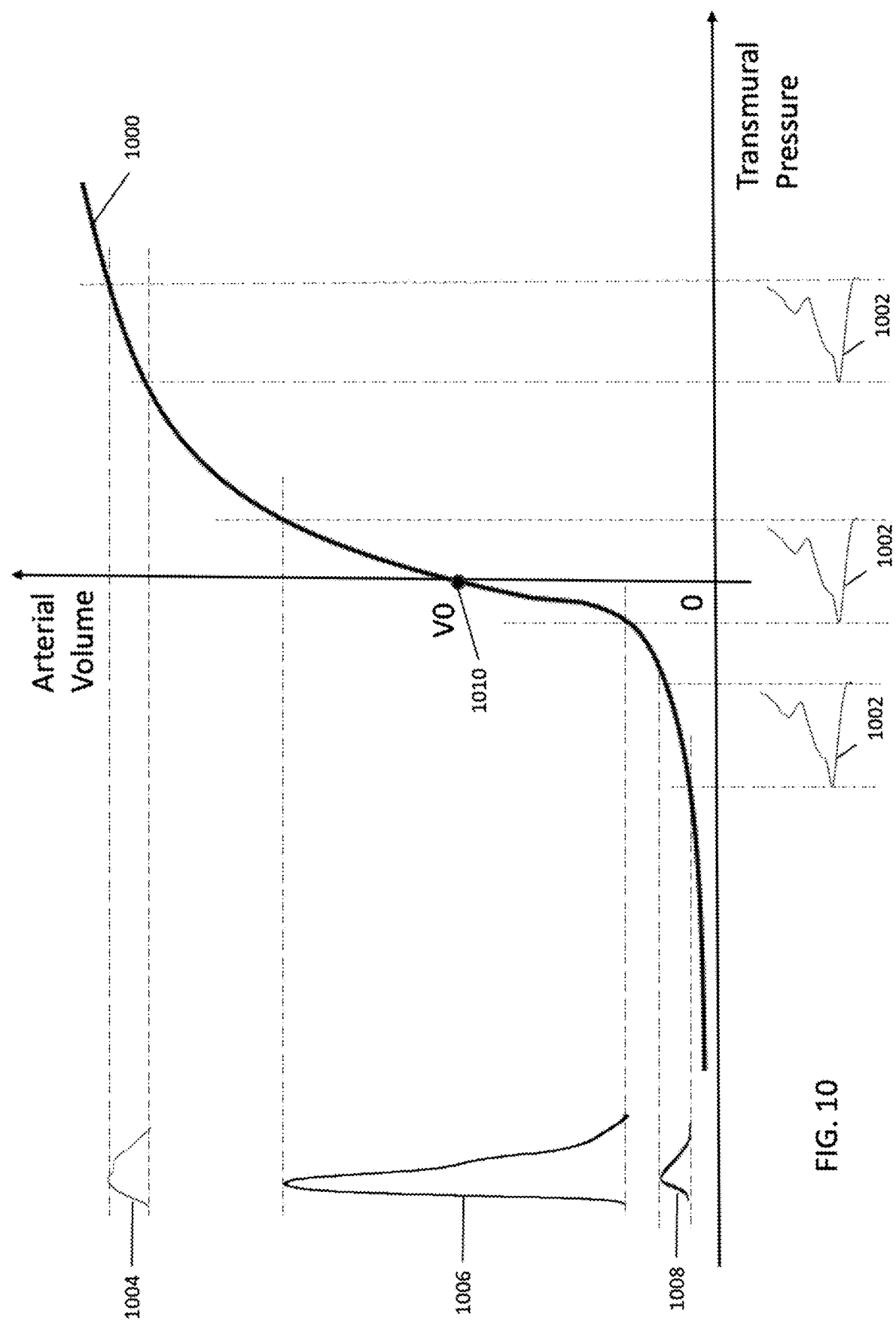
FIG. 10 is a graph showing the mechanical properties of an artery.

FIG. 10 is a graph showing the mechanical properties of an artery. The graph in FIG. 10 shows the relationship between the transmural pressure on the horizontal axis and the arterial volume V on the vertical axis, where the transmural pressure is defined as the arterial pressure subtracted by the cuff pressure. As shown in this graph, the mechanical properties of an artery 1000 generally show strong nonlinearity. The waveform 1002 indicates one arterial pressure waveform as the input at three different locations, When the transmural pressure equals 0 at an equilibrium state, that is, when the arterial wall is unloaded, the artery compliance, as the amount of change in volume due to pulsatility, will be maximized as shown by 1006. When the transmural pressure is greater or lesser than 0, the artery compliance is reduced, and the waveform shape of the arterial volume is also different, as shown by volume waveforms 1004 and 1008. Therefore, the point where transmural pressure is 0 is significant, because it indicates where the arterial pressure can be directly measured by measuring the cuff pressure. Identifying the transmural pressure zero point is the key to the blood pressure measurement.

Figure 11:
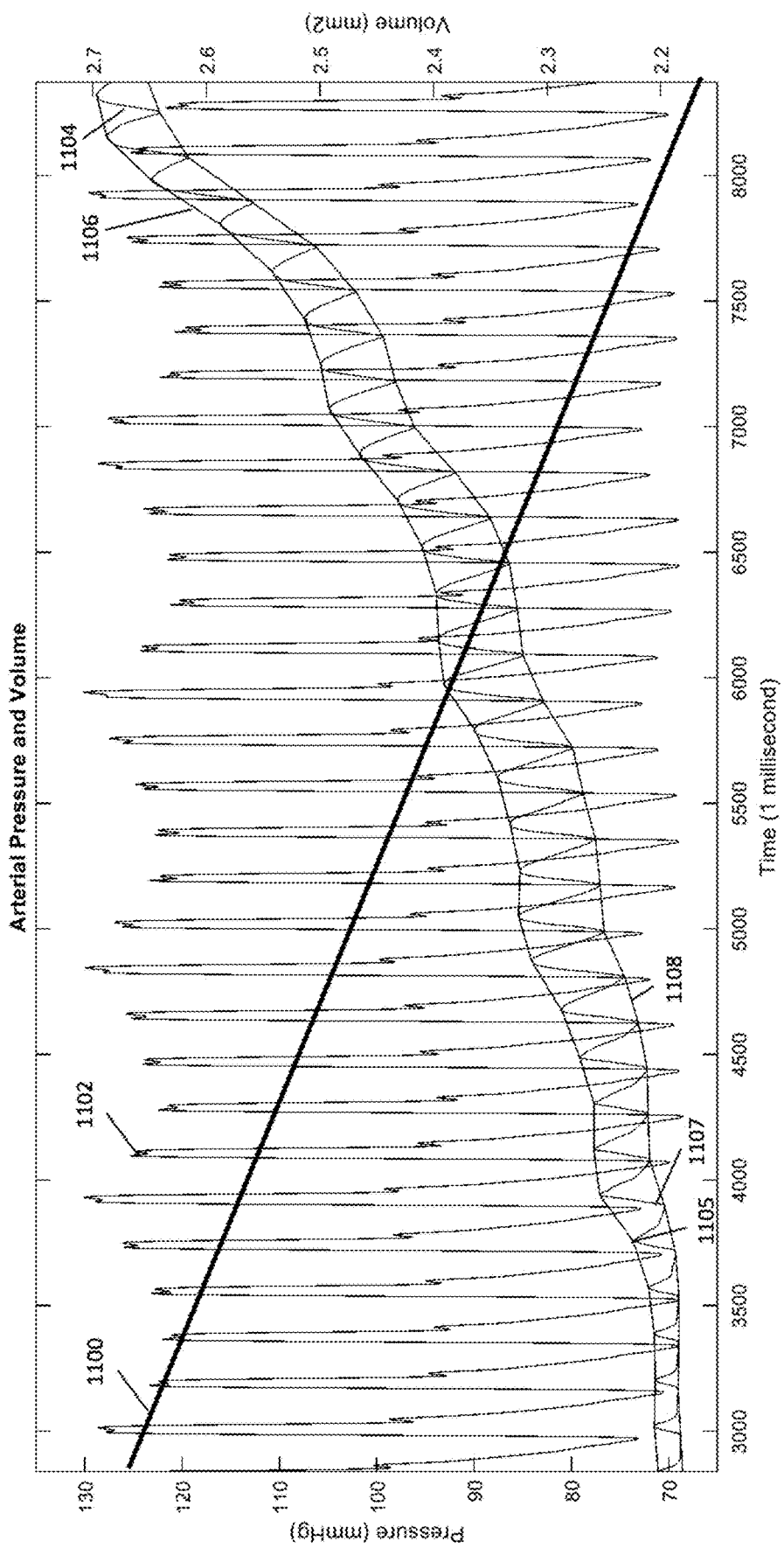
FIG. 11 is an arterial pressure and volume chart describing their relationship during the deflation process, according to one or more embodiments of the present invention.

FIG. 11 is an arterial pressure and volume chart describing their relationship during the deflation process, according to one or more embodiments of the present invention. Referring to FIG. 11, the cuff pressure during the deflation is 1100 as an abstract representation of either 902 or 904, the arterial pressure is marked by the waveform 1102, and the arterial volume is marked by the waveform 1104. The systolic volume during each heartbeat is marked by the volume peak of 1105. Connecting all peaks of the volume waveform forms its contour 1106, representing the relationship between the cuff pressure, the systolic pressure, and the arterial volume. The contour 1106 bears the features of curve 1000. The diastolic volume during each heartbeat is marked by the volume valley 1107. Connecting all valleys of the volume waveform forms its contour 1108, representing the relationship between the cuff pressure, the diastolic pressure, and the arterial volume. The contour 1108 bears the features of the curve 1000. Although the contours 1106 and 1108 are in FIG. is built as the piecewise linear functions, they can be quadratic functions, cubic splines, and any other functions.

Building the relationship of arterial pressures and volume during the deflation phase is a preferred embodiment. The same process can be used for building the same relationship during the inflation phase as another embodiment, with the sign change for the cuff pressure.

Normally referring to the systolic and diastolic pressures, one assumption is they are the constants during a reasonably short period. However, FIG. 11 indicates it is often not true, where arterial pressure 1102 shows a periodic change, due to the subject's breathing. Therefore, to derive volume contours as the artery mechanical properties, the breathing effect needs to be removed.

Figure 12:
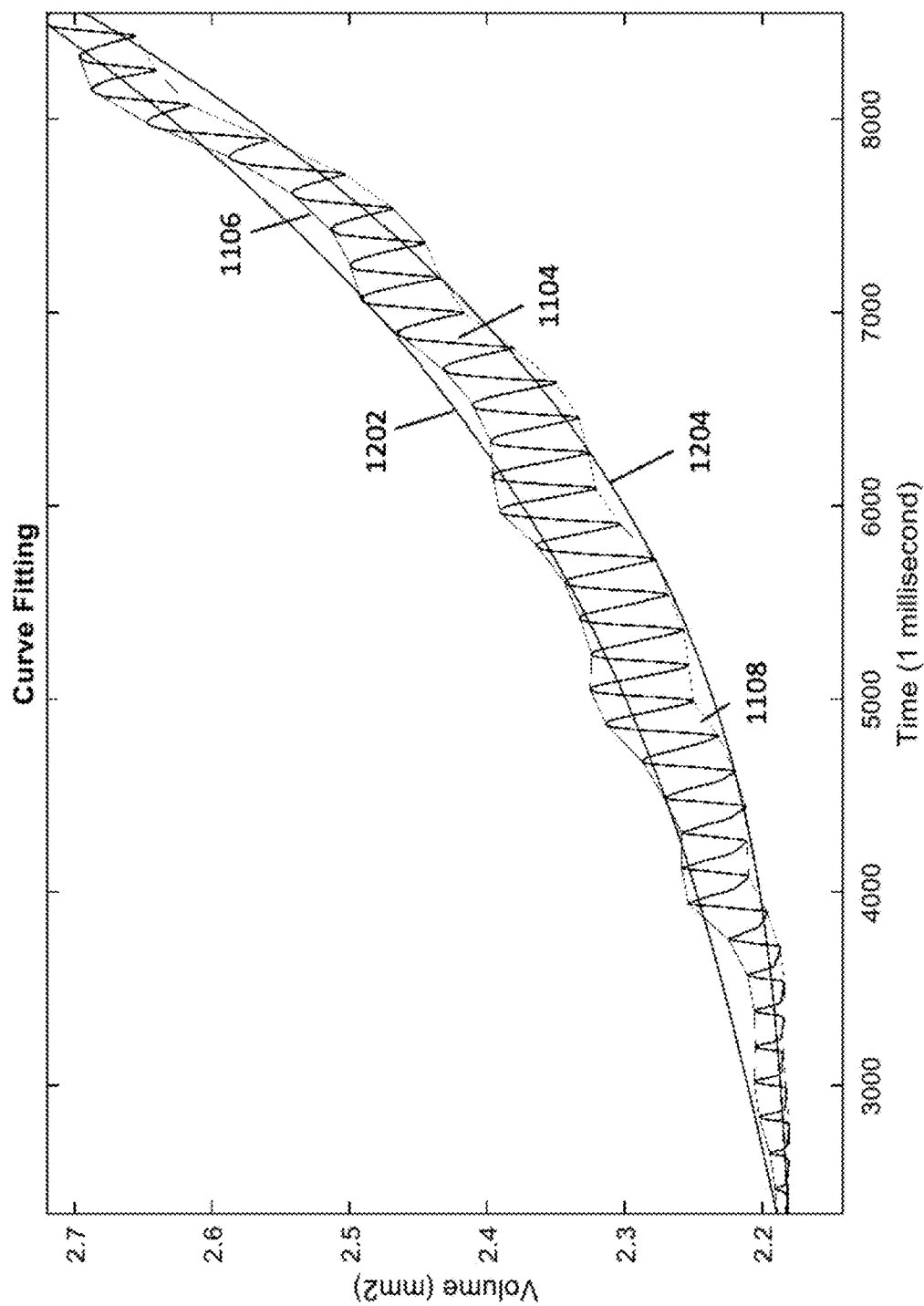
FIG. 12 is a curve-fitting chart describing the noise removal process for the arterial volume signal, according to one or more embodiments of the present invention.

FIG. 12 is a curve-fitting chart describing the breathing noise removal process for the arterial volume signal, according to one or more embodiments of the present invention. Since the contours 1106 and 1108 are distorted by the subject' breathing, it is necessary to remove the breathing component which is denoted as a sinusoidal function $$Fb=k\times\sin(2\times(\alpha\ xi+\beta))$$

Where k, $\alpha$, and $\beta$ are parameters, and xi is the time series at the systolic or diastolic peaks.

If fitting the contour with a polynomial. While the polynomial can be any order, a cubic function is chosen to illustrate the process.

$$Fp=p3\ xi^3+p2\ xi^2+p1\ xi+p0$$

Denote the parameter vector u={p3, p2, p1, p0, k, $\alpha$, $\beta$}, the error function at xi can be written as $$F(u)=Fp-(yi-Fb)$$

Optimize F (u) in the least square sense, then a vector u can be obtained. The final fitting function for the arterial volume can be written as $$F=Fp+Fb$$

Which are shown in FIG. 12 by 1202 for systolic and 1204 for diastolic. It should be pointed out the contours can be fit with other functions as well, such as piecewise exponential or arctangent functions. In these cases, the parameter vector will change accordingly, with the appropriate parameters to replace polynomial parameters p3, p2, p1, and p0.

Figure 13:
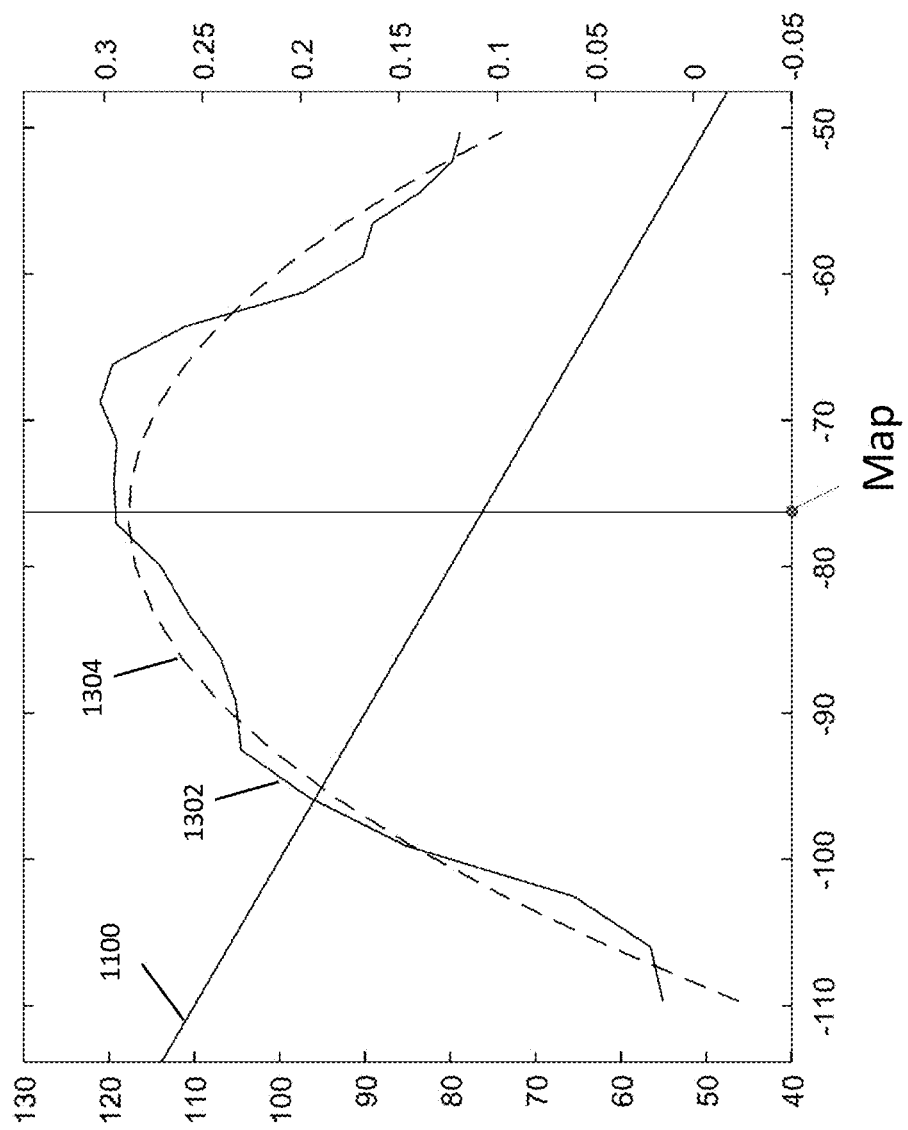
FIG. 13 is a deflation pressure and volume change chart describing the process for the mean arterial pressure (MAP) measurement process, according to one or more embodiments of the present invention.

FIG. 13 is a deflation pressure and volume change chart describing the process for the mean arterial pressure measurement process, according to one or more embodiments of the present invention. Referring to FIG. 13, curve 1302 is the volume change between the systolic and diastolic pressures. In one embodiment it can be obtained by subtracting the contour 1204 from the contour 1202 in FIG. 12. Another embodiment is defined as the following. In FIG. 9, drawing a line 928 connects two adjacent diastolic valleys in volume waveform 910. Then draw a vertical line through the systolic peak in volume waveform 910 between the two adjacent diastolic valleys. Line segment 926 bounded by the systolic peak and line 928, is Sys_vol_lin. Extending line segment 926 to intersect to the cuff pressure waveform 904, generates the cuff pressure for Sys_vol_lin 928. Repeat the process for all systolic peaks of the volume waveform 910, a contour 1302 in FIG. 13 is formed. Then using a quadratic curve fitting generates the curve 1304, whose maximum is located at the mean arterial pressure.

Finding the mean arterial pressure during the deflation phase is a preferred embodiment. The same process can be used for finding the mean arterial pressure during the inflation phase as another embodiment, with the sign change for the cuff pressure.

Figure 14:
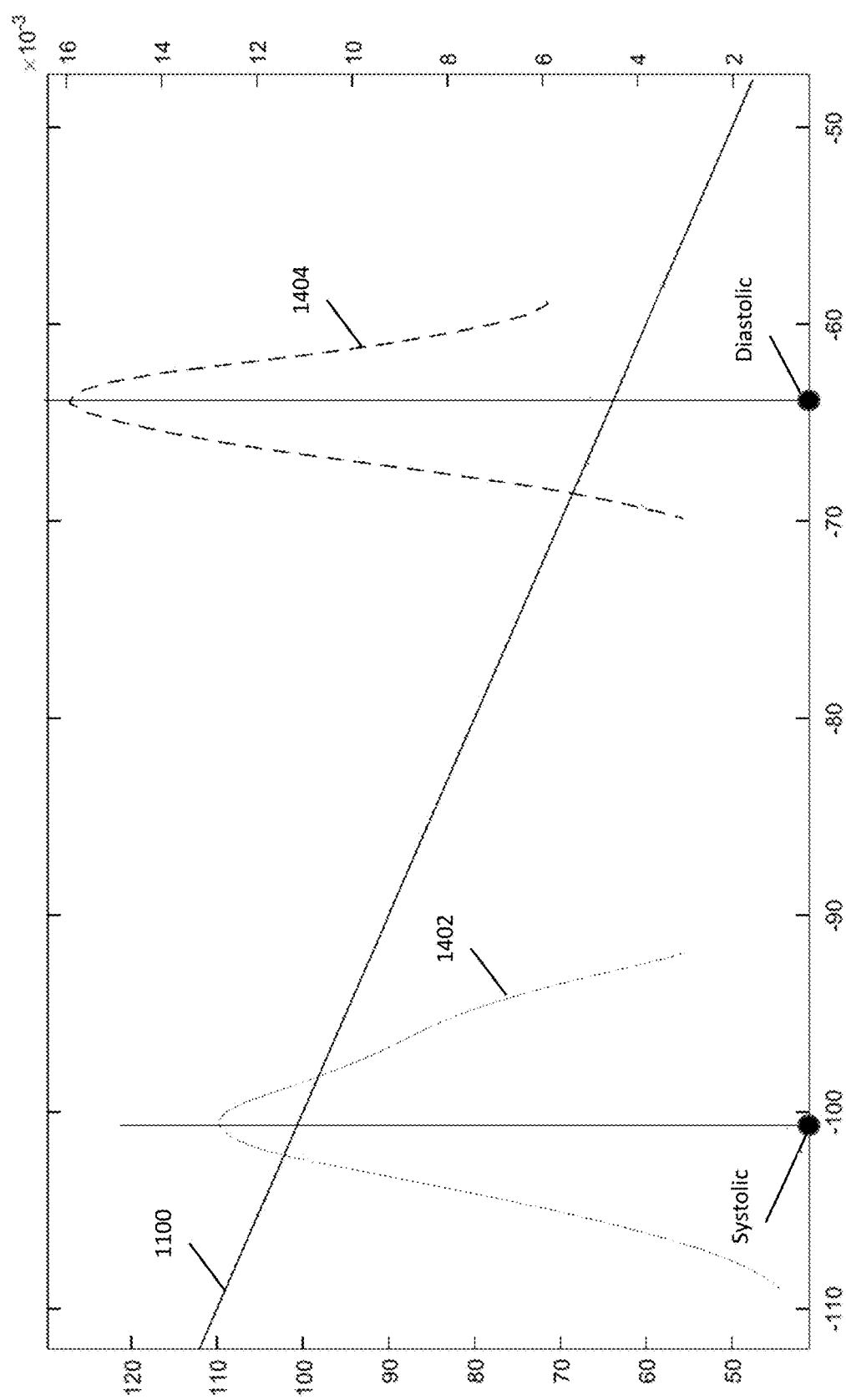
FIG. 14 is a deflation pressure and finite-difference of pressure-volume relationship chart describing the systolic and diastolic pressure measurement process, according to one or more embodiments of the present invention.

FIG. 14 is a deflation pressure and finite-difference of pressure-volume relationship chart describing the systolic and diastolic pressure measurement process, according to one or more embodiments of the present invention. Referring to FIG. 14, the curves 1402 and 1404 are the finite-differences curves measured from a subject, which is equivalent to the finite-difference of the artery mechanical property shown in FIG. 10, for the systolic and diastolic pressure respectively. The point V0 1010 in FIG. 10 is defined by the maximum of 1402 and 1404, for systolic and diastolic. The pressures where the maximum is located, indicate the systolic and diastolic pressure respectively.

Finding the systolic and diastolic pressures during the deflation phase is a preferred embodiment. The same process can be used for finding the systolic and diastolic pressures during the inflation phase as another embodiment, with the sign change for the cuff pressure.

One important parameter is V0 1010 for the mean arterial pressure, which can be used as the controller set point for arterial pressure tracking. The following process describes how to drive it. Denote V0s for systolic, V0d for diastolic, V0m for MAP, then $$V0m=V0d+(V0s-V0d)/(\text{Systolic}-\text{Diastolic})\times(\text{MAP}-\text{Diastolic})$$

The invention claimed is:

1. An optical-based oscillometric blood pressure measurement device for measuring arterial blood pressure, comprising: a cuff that is configured to fit on a blood pressure measurement site to compress an artery of the measurement site; an inflation/deflation unit that consists of a piezoelectric pump and a valve, to increase and decrease a pressure inside the cuff; a pressure detection unit that detects a cuff pressure, which is the pressure inside the cuff; one or more light-emitting diode and photodiode pairs, to generate plethysmogram; a volume detection unit that detects an arterial volume signal indicating a volume of the artery per unit length; a control unit that sets the cuff pressure by controlling the inflation/deflation unit; and an extraction unit that extracts the relationship of the arterial volume with a transmural pressure as defined by the difference between the arterial pressure and the cuff pressure, wherein the extraction unit measures the volume and pressure waveforms to detect systolic, diastolic, and the mean arterial pressure for each heartbeat of a subject, wherein the pressure waveforms are derived from a starting point, a flat phase, a ramp up phase, and a stop point; and wherein the extraction unit is configured to utilize a curve fitting method for performing a breathing noise removal process for eliminating noises introduced by breathing by the subject, wherein the breathing noise removal process is performed by a sinusoidal function Fb=k×sin(2π($\alpha$ xi+$\beta$)), wherein k, $\alpha$, and $\beta$ are parameters required to define the sinusoidal function, and xi is a time series at systolic or diastolic peaks.

2. The optical-based oscillometric blood pressure measurement device of claim 1, wherein the measurement site includes at least one of the subjects' fingers, wrist, arm, or ankle.

3. The optical-based oscillometric blood pressure measurement device of claim 1, wherein the valve comprises at least one of a piezoelectric valve, a solenoid valve, an electromechanical valve, or a fixed orifice to release pneumatic pressure in an air bag of the cuff, and wherein pneumatic pressure is modulated by the pump.

4. The optical-based oscillometric blood pressure measurement device of claim 1, wherein the light-emitting diode and photodiode pairs can be single or plural, and the total numbers of the light-emitting diode and the total numbers of the photodiodes can be unequal.

5. The optical-based oscillometric blood pressure measurement device of claim 1, wherein the volume detection unit, control unit, and extraction unit operate in the CPU of a microcontroller, whose input channels comprises of digit input channels and/or analog to digital (ADC) input channels, and whose output channels of comprises analog output channels and/or digital to analog (DAC) output channels.

6. A volume detection method of detecting the volume signal for an optical-based oscillometric blood pressure measurement device for measuring blood pressure, comprising: a cuff that is configured to fit on a blood pressure measurement site to compress an artery of the measurement site; an inflation/deflation unit that consists of a piezoelectric pump and a valve, to increase and decrease a pressure inside the cuff; a pressure detection unit that detects a cuff pressure, which is the pressure inside the cuff; one or more light-emitting diode and photodiode pairs, to generate plethysmogram; volume detection unit that detects an arterial volume signal indicating a volume of the artery per unit length, where the volume detection method further comprises providing a negative logarithm method, a LED/photodiode driver adjusting method, and a heartbeat detection method; a control unit that set the cuff pressure by controlling the inflation/deflation unit; and providing an extraction unit that extracts the relationship of the arterial volume with a transmural pressure as defined by the difference between the arterial pressure and the cuff pressure, wherein the extraction unit measures the volume and pressure waveforms to detect systolic, diastolic, and the mean arterial pressure of each heartbeat of a subject; wherein the pressure waveforms are derived from a starting point, a flat phase, a ramp up phase, and a stop point; and wherein the extraction unit is configured to utilize a curve fitting method for performing a breathing noise removal process for eliminating noises introduced by breathing by the subject, wherein the breathing noise removal process is performed by a sinusoidal function $Fb = k \times \sin(2\pi(\alpha \; xi + \beta))$, wherein $k$, $\alpha$, and $\beta$ are parameters required to define the sinusoidal function, and $xi$ is a time series at systolic or diastolic peaks.

7. The volume detection method of claim 6, wherein the negative logarithm method converts the plethysmogram into an arterial volume signal per unit length by subtracting from a system constant and logarithm conversion.

8. The volume detection method of claim 6, wherein the LED/photodiode driver adjusting method adjusts the LED driver constants whether they are gains or ADCs, or Photodiode driver constants whether they are gains or DACs, to achieve the maximum signal to noise ratio of volume signal.

9. The volume detection method of claim 6, wherein the heartbeat detection method identifies each heartbeat real-time in the volume waveform, with its systolic peak value and time, diastolic valley value and time, and the heartbeat rate.

10. A control method of controlling of an optical-based oscillometric blood pressure measurement device for measuring blood pressure, comprising: a cuff that is configured to fit on a blood pressure measurement site to compress an artery of the measurement site; an inflation/deflation unit that consists of a piezoelectric pump and a valve, to increase and decrease a pressure inside the cuff; a pressure detection unit that detects a cuff pressure, which is the pressure inside the cuff; one or more light emitting diode and photodiode pairs, to generate plethysmogram; a volume detection unit that detects an arterial volume signal indicating a volume of the artery per unit length; the method comprising providing a control unit that sets the cuff pressure by controlling the inflation/deflation unit, with a model-based predictive controller, a two-degree of freedom Proportional integral, and differential (PID) controller, a ramp up controller, and ramp down controller; and an extraction unit that extracts the relationship of the arterial volume with a transmural pressure as defined by the difference between the arterial pressure and the cuff pressure, wherein the extraction unit measures the volume and pressure waveforms to detect systolic, diastolic, and the mean arterial pressure of a each heartbeat of a subject; wherein the pressure waveforms are derived from a starting point, a flat phase, a ramp up phase, and a stop point; and wherein the extraction unit is configured to utilize a curve fitting method for performing a breathing noise removal process for eliminating noises introduced by breathing by the subject, wherein the breathing noise removal process is performed by a sinusoidal function $Fb = k \times \sin(2\pi(\alpha \; xi + B))$, wherein $k$, $\alpha$, and $\beta$ are parameters required to define the sinusoidal function, and $xi$ is a time series at systolic or diastolic peaks.

11. The control method of claim 10, wherein the model-based predictive controller includes pump and valve models, which are nonlinear, and describes the relationship between the required cuff pressure and the pump/valve driver parameters wherein, for any cuff pressure, the model outputs the estimated pump DAC and valve DAC or their gains.

12. The control method of claim 10, wherein the two-degree of freedom Proportional, integral, and differential (PID) controller provides the final control outputs to eliminate the linear portion of the control errors.

13. The control method of claim 10, wherein the ramp-up controller calculates the inflation pressure slope and start/stop pressures.

14. The control method of claim 10, wherein the ramp-down controller calculates the deflation pressure slope and start/stop pressures.

15. An extraction method of measuring the arterial pressures of a subject for an optical-based oscillometric blood pressure measurement device for measuring blood pressure, comprising: a cuff that is configured to fit on a blood pressure measurement site to compress an artery of the measurement site; an inflation/deflation unit that consists of a piezoelectric pump and a valve, to increase and decrease a pressure inside the cuff; a pressure detection unit that detects a cuff pressure, which is the pressure inside the cuff; one or more light emitting diode and photodiode pairs, to generate plethysmogram; volume detection unit that detects an arterial volume signal indicating a volume of the artery per unit length; a control unit that set the cuff pressure by controlling the inflation/deflation unit; and extraction unit that extracts the relationship of the arterial volume with a transmural pressure as defined by the difference between the arterial pressure and the cuff pressure, wherein the extraction unit measures the volume and pressure waveforms to detect systolic, diastolic, and the mean arterial pressure of a subject; wherein the pressure waveforms are derived from a starting point, a flat phase, a ramp up phase, and a stop point; and wherein the extraction unit is configured to utilize a curve fitting method for performing a breathing noise removal process for eliminating noises introduced by breathing by the subject, wherein the breathing noise removal process is performed by a sinusoidal function $Fb = k \times \sin(2\pi(\alpha \; xi + B))$, wherein $k$, $\alpha$, and $\beta$ are parameters required to define the sinusoidal function, and $xi$ is a time series at systolic or diastolic peaks, the method comprising providing a pressure-volume curve building method, a curve fitting method, a mean arterial pressure (MAP) computation method, a systolic/diastolic extraction method, and an arterial unloading value calculation method.

16. The extraction method of claim 15, wherein the pressure-volume curve building method uses the volume waveform and the deflation pressure, to derive the pressure and arterial volume relationship.

17. The extraction method of claim 15, wherein the curve fitting method eliminates the noises introduced by breathing by removing breathing effects from the systolic volume contour measured by the extraction unit.

18. The extraction method of claim 15, wherein the mean arterial pressure computation method derives the mean arterial pressure using the volume change due to systolic and diastolic pressure and eliminates the noise using a quadratic curve fitting wherein finding the location of the maximum of the curve gives the MAP.

19. The extraction method of claim 15, wherein the systolic/diastolic extraction method uses the finite-difference of the pressure and arterial volume relationship to identify their maximums, and thus to find the systolic and diastolic pressures of a subject.

20. The extraction method of claim 15, wherein the arterial unloading value calculation method calculates the unloading point of volume, where the transmural pressure equals zero.

\* \* \* \* \*

UNITED STATES PATENT AND TRADEMARK OFFICE
CERTIFICATE OF CORRECTION

| | | |
|---|---|---|
| PATENT NO. | : 12,350,025 B1 | Page 1 of 1 |
| APPLICATION NO. | : 17/517283 | |
| DATED | : July 8, 2025 | |
| INVENTOR(S) | : Sharon Xiaorong Wang, Jason Andrew Chen and William Barry Chen-Mertens | |

It is certified that error appears in the above-identified patent and that said Letters Patent is hereby corrected as shown below:

On the Title Page

In the assignee information, 'JB Health Tech' should be corrected to 'JB HealthTech,'.

Signed and Sealed this
Fifth Day of August, 2025

Coke Morgan Stewart
*Acting Director of the United States Patent and Trademark Office*